United States Patent
Fujita et al.

(10) Patent No.: US 10,352,862 B2
(45) Date of Patent: Jul. 16, 2019

(54) RAMAN SPECTROSCOPIC MICROSCOPE AND RAMAN SCATTERED LIGHT OBSERVATION METHOD

(71) Applicant: NANOPHOTON CORPORATION, Osaka (JP)

(72) Inventors: Katsumasa Fujita, Osaka (JP); Satoshi Kawata, Osaka (JP); Kozue Watanabe, Osaka (JP)

(73) Assignee: NANOPHOTON CORPORATION, Osaka (JP)

( * ) Notice: Subject to any disclaimer, the term of this patent is extended or adjusted under 35 U.S.C. 154(b) by 93 days.

(21) Appl. No.: 15/504,957

(22) PCT Filed: Aug. 18, 2015

(86) PCT No.: PCT/JP2015/004097
§ 371 (c)(1),
(2) Date: Feb. 17, 2017

(87) PCT Pub. No.: WO2016/027453
PCT Pub. Date: Feb. 25, 2016

(65) Prior Publication Data
US 2017/0276610 A1     Sep. 28, 2017

(30) Foreign Application Priority Data
Aug. 18, 2014 (JP) ................. 2014-165760

(51) Int. Cl.
*G01N 21/65* (2006.01)
*G01J 3/44* (2006.01)
(Continued)

(52) U.S. Cl.
CPC ............. *G01N 21/65* (2013.01); *G01J 3/44* (2013.01); *G02B 21/0032* (2013.01); *G02B 27/58* (2013.01)

(58) Field of Classification Search
CPC .................................. G01N 21/65; G01J 3/44
See application file for complete search history.

(56) References Cited

U.S. PATENT DOCUMENTS

| | | | |
|---|---|---|---|
| 2003/0132394 A1 | 7/2003 | Wolleschensky et al. | |
| 2004/0113059 A1* | 6/2004 | Kawano | G02B 21/002 250/234 |

(Continued)

FOREIGN PATENT DOCUMENTS

| | | |
|---|---|---|
| EP | 1248132 | 10/2002 |
| JP | 2002-323660 | 11/2002 |

(Continued)

OTHER PUBLICATIONS

Palonpon, Almar F., et al.: "Raman and SERS microscopy for molecular imaging of live cells," Nature Protocols, vol. 8(4), pp. 677-692, 2013.

(Continued)

*Primary Examiner* — Maurice C Smith
(74) *Attorney, Agent, or Firm* — Seyfarth Shaw LLP

(57) ABSTRACT

In a Raman spectroscopic microscope, a spatial resolution that exceeds the diffraction limit of light is achieved. A diffraction grating diffracts laser light emitted from a light source and thereby generates diffracted light. A spectroscope acquires a spectrum of incident light and a spatial distribution of light intensities of the spectrum. An optical system applies interference light formed by +1st order diffracted light and −1st order diffracted light generated in the diffraction grating to an object to be observed as linear illumination light and guides a Raman scattered light generated by the application of the linear illumination light to the object to be observed to the spectroscope, the linear illumination light having its longitudinal direction in a first direction. A control unit controls the optical system and thereby scans the object (Continued)

to be observed by the linear illumination light in a second direction.

16 Claims, 18 Drawing Sheets

(51) Int. Cl.
*G02B 21/00* (2006.01)
*G02B 27/58* (2006.01)

(56) References Cited

U.S. PATENT DOCUMENTS

| | | | |
|---|---|---|---|
| 2005/0259266 A1* | 11/2005 | Seko | G01B 11/02 356/498 |
| 2007/0057168 A1* | 3/2007 | Imai | G01D 5/34715 250/231.13 |
| 2007/0132994 A1* | 6/2007 | Kobayashi | G01J 3/02 356/328 |
| 2008/0076985 A1* | 3/2008 | Matousek | A61B 5/0059 600/310 |
| 2010/0157422 A1* | 6/2010 | Ouchi | G02B 21/14 359/385 |
| 2013/0027703 A1* | 1/2013 | Shau | G01N 21/3504 356/364 |
| 2014/0320957 A1 | 10/2014 | Ouchi et al. | |

FOREIGN PATENT DOCUMENTS

| | | |
|---|---|---|
| JP | 2006-258990 | 9/2006 |
| WO | WO 2013/108626 | 7/2013 |

OTHER PUBLICATIONS

Extended European Search Report issued in European patent application No. 15833847.5 dated Mar. 12, 2018.
Gustafsson, M.G.L.: "Surpassing the lateral resolution limit by a factor of two using structured illumination microscopy", Journal of Microscopy, vol. 198(2), May 2000, pp. 82-87.
Kim, Taejoong, et al.: "Enhancemetn of fluorescence confocal scanning microscopy lateral resolution by use of structured illumination", Measurement Science and Technology, vol. 20, 2009.
Mandula, Ondrej, et al.: "Line scan-structured illumination microscopy super-resolution imaging in thick fluorescent samples", Optics Express, vol. 20(22), Oct. 22, 2012.

* cited by examiner

COMPARATIVE EXAMPLE 1
SLIT-CONFOCAL RAMAN
SPECTROSCOPIC MICROSCOPE

EXAMPLE 1

RAMAN SPECTROSCOPIC MICROSCOPE AND RAMAN SCATTERED LIGHT OBSERVATION METHOD

CROSS REFERENCE TO RELATED APPLICATIONS

This application is a U.S. National Stage application of PCT International Patent Application Number PCT/JP2015/004097, which was filed on Aug. 18, 2015, which claims priority to Japanese Patent Application No. JP2014-165760, which was filed on Aug. 18, 2014, the disclosures of each of which is incorporated herein by reference in its entirety.

TECHNICAL FIELD

The present invention relates to a Raman spectroscopic microscope and a Raman scattered light observation method.

BACKGROUND ART

As a technique for observing a micro-structure of an object to be observed, a Raman spectroscopic microscope has been known. Since the Raman spectroscopic microscope can acquire a spatial distribution of molecules or crystal lattices while measuring the frequency of their vibrations, it can be applied to a wide range of technical fields such as material engineering, medical diagnoses, and drug discoveries. In general, the spatial resolution of an observation is restricted by the wave nature of illumination light in such optical observation techniques.

As a technique for improving the spatial resolution, use of structured illumination (e.g., Patent Literature 1) has been known. Further, it has been reported that as a technique for improving the spatial resolution, use of linear illumination (or line illumination) is effective (e.g., Non-patent Literature 2 and 3). These literatures also propose a technique for improving the spatial resolution of a fluorescence microscope by combining results of observations in which the irradiation place of illumination light is shifted (Non-patent Literature 1, 2 and 3).

CITATION LIST

Patent Literature

Patent Literature 1: International Patent Publication No. WO2013/108626

Non Patent Literature

Non-patent Literature 1: M. G. L. Gustafsson, "Surpassing the lateral resolution limit by a factor of two using structured illumination microscopy", 2000, Journal of Microscopy, vol. 198, Issue 2, pp. 82-87

Non-patent Literature 2: Taejoong Kim, et al., "Enhancement of fluorescence confocal scanning microscopy lateral resolution by use of structured illumination", 2009, Measurement Science and Technology, Volume 20, 055501

Non-patent Literature 3: Ondrej Mandula, et al., "Line scan-structured illumination microscopy super-resolution imaging in thick fluorescent samples", 8 Oct. 2012, OPTICS EXPRESS, Vol. 20, No. 22, pp. 24168-24174

SUMMARY OF INVENTION

Technical Problem

However, the inventor has found that there is the following problem in the above-described techniques. The above-described techniques do not mention any improvement in the spatial resolution of an observation by a Raman spectroscopic microscope. Therefore, it is unclear how the spatial resolution of an observation can be improved in the Raman spectroscopic microscope.

The present invention has been made in view of the above-described circumstance and an object thereof is to achieve a spatial resolution that exceeds the limit of diffraction (hereinafter referred to as a "diffraction limit") of light in a Raman spectroscopic microscope.

Other objects and novel features will be more apparent from the following description in the specification and the accompanying drawings.

Solution to Problem

A Raman spectroscopic microscope according to a first aspect of the present invention includes: a light source; a diffraction device configured to diffract light emitted from the light source and thereby generate diffracted light; a spectroscope configured to acquire a spectrum of incident light and a spatial distribution of light intensities of the spectrum; an optical system configured to apply interference light formed by +1st order diffracted light and −1st order diffracted light generated in the diffraction device to an object to be observed as linear illumination light and guide a Raman scattered light generated by the application of the linear illumination light to the object to be observed to the spectroscope, the linear illumination light having its longitudinal direction in a first direction perpendicular to interference fringes formed by the interference light; and a control unit configured to scan the object to be observed by the linear illumination light in a second direction appendicular to the first direction. In this way, it is possible to form interference fringes of the +1 st and −1st order diffracted lights in the first direction of the linear illumination light. As a result, it is possible to increase the spatial frequency resolvable in the first direction beyond the diffraction limit of light.

A Raman spectroscopic microscope according to a second aspect of the present invention is the above-described Raman spectroscopic microscope, in which the control unit scans the object to be observed by the linear illumination light in such a manner that a sampling interval in the second direction coincides with a spatial frequency appearing in an intensity distribution in the first direction of the linear illumination light. In this way, it is possible to acquire a two-dimensional (hereinafter referred to as "2D") image of the object to be observed in which the spatial frequency in the first direction coincides with that in the second direction.

A Raman spectroscopic microscope according to a third aspect of the present invention is the above-described Raman spectroscopic microscope, in which the spectroscope includes: a slit on which the Raman scattered light is incident; and an image pickup device configured so that the Raman scattered light that enters the image pickup device through the slit forms an image on an image pickup surface thereof, and a spectrum of the Raman scattered light and a spatial distribution of light intensities of the spectrum are acquired by performing an image-shooting by the image pickup device. In this way, it is possible to simultaneously acquire Raman scattered light coming from a linear illumination part.

A Raman spectroscopic microscope according to a fourth aspect of the present invention is the above-described Raman spectroscopic microscope, in which the control unit changes a phase of the interference fringes formed by the interference light formed by the +1st and −1st order diffracted lights in a multi-step manner while maintaining an irradiation place of the linear illumination light with respect to the object to be observed, and the control unit generates a spatial distribution of light intensities of a spectrum in the irradiation place by combining spatial distributions of light intensities of a plurality of spectrums, each of the plurality of spectrums being obtained for a respective one of the changed phases of the interference fringes. In this way, it is possible to further improve the spatial resolution in the first direction in the 2D image of the object to be observed.

A Raman spectroscopic microscope according to a fifth aspect of the present invention is the above-described Raman spectroscopic microscope, in which the control unit acquires a spatial distribution of light intensities of the spectrum of the Raman scattered light acquired by the spectroscope, and the control unit corrects a spatial pitch of the spatial distribution of light intensities so that a spatial frequency appearing in the spatial distribution of light intensities becomes uniform. In this way, it is possible to correct a distortion in the spatial distribution of light intensities of the spectrum of the Raman scattered light acquired by the spectroscope caused by an aberration of the spectroscope and thereby to acquire an accurate 2D image of the object to be observed.

A Raman spectroscopic microscope according to a sixth aspect of the present invention is the above-described Raman spectroscopic microscope, in which the control unit: divides the spatial distribution of light intensities acquired by the spectroscope into a plurality of sections; acquires a spatial frequency appearing in a spatial distribution of light intensities for each of the plurality of sections; corrects a spatial pitch of the spatial distribution of light intensities for each of the plurality of sections so that a spatial frequency of each of the plurality of sections becomes equal to a reference value; and corrects the spatial distribution of light intensities of the spectrum by combining the spatial-pitch-corrected spatial distributions of light intensities of the plurality of sections. In this way, it is possible to correct a spatial pitch of each section based on a spatial frequency of each section in a concrete manner.

A Raman spectroscopic microscope according to a seventh aspect of the present invention is the above-described Raman spectroscopic microscope, in which the light that is emitted from the light source and is incident on the diffraction device is collimated light. In this way, it is possible to prevent light having a large light intensity emitted from the light source used for the Raman spectroscopy from converging in the diffraction device and thereby to prevent the diffraction device from deteriorating.

A Raman spectroscopic microscope according to an eighth aspect of the present invention is the above-described Raman spectroscopic microscope, in which a phase and an intensity of 0th order diffracted light generated in the diffraction device are adjusted with respect to a phase of the +1st and −1st order diffracted lights, and the +1st and −1st order diffracted lights and the 0th order diffracted light are thereby made to interfere with each other so that interference fringes are formed in a depth direction of a sample. In this way, it is possible to form interference fringes in the depth direction of the sample and thereby to improve the spatial resolution in the depth direction of the sample.

A Raman spectroscopic microscope according to a ninth aspect of the present invention is the above-described Raman spectroscopic microscope, further including a beam cross-section converter disposed between the light source and the diffraction device or in the optical system, the beam cross-section converter being configured to change a shape of a beam cross-section of light passing therethrough. In this way, it is possible to make desired diffracted light incident on a pupil of an objective lens, through which illumination light is applied to a sample, even when the number of grooves in the diffraction device is fixed.

A Raman scattered light observation method according to a tenth aspect of the present invention includes: diffracting light emitted from a light source by a diffraction device and thereby generating diffracted light; applying interference light formed by +1st order diffracted light and −1st order diffracted light generated in the diffraction device to an object to be observed as linear illumination light having its longitudinal direction in a first direction perpendicular to interference fringes formed by the interference light; scanning the object to be observed by the linear illumination light in a second direction appendicular to the first direction; and acquiring a spectrum of Raman scattered light generated by the application of the linear illumination light to the object to be observed and a spatial distribution of light intensities of the spectrum. In this way, it is possible to form interference fringes of the +1st and −1st order diffracted lights in the first direction of the linear illumination light. As a result, it is possible to increase the spatial frequency resolvable in the first direction beyond the diffraction limit of light.

A Raman scattered light observation method according to an eleventh aspect of the present invention is the above-described Raman scattered light observation method, in which the object to be observed is scanned by the linear illumination light in such a manner that a sampling interval in the second direction coincides with a spatial frequency appearing in an intensity distribution in the first direction of the linear illumination light. In this way, it is possible to acquire a 2D image of the object to be observed in which the spatial frequency in the first direction coincides with that in the second direction.

A Raman scattered light observation method according to a twelfth aspect of the present invention is the above-described Raman scattered light observation method, in which the Raman scattered light is made incident on a slit, an image is formed on an image pickup surface of an image pickup device by the Raman scattered light that enters the image pickup device through the slit, and a spectrum of the Raman scattered light and a spatial distribution of light intensities of the spectrum are acquired by performing an image-shooting by the image pickup device. In this way, it is possible to simultaneously acquire Raman scattered light coming from a linear illumination part.

A Raman scattered light observation method according to a thirteenth aspect of the present invention is the above-described Raman scattered light observation method, in which a phase of the interference fringes formed by the interference light formed by the +1st and −1st order diffracted lights is changed in a multi-step manner while maintaining an irradiation place of the linear illumination light with respect to the object to be observed, and a spatial distribution of light intensities of a spectrum in the irradiation place is generated by combining spatial distributions of light intensities of a plurality of spectrums, each of the plurality of spectrums being obtained for a respective one of the changed phases of the interference fringes. In this way, it is possible to further improve the spatial resolution in the first direction in the 2D image of the object to be observed.

A Raman scattered light observation method according to a fourteenth aspect of the present invention is the above-described Raman scattered light observation method, in which a spatial pitch of the spatial distribution of light intensities of the spectrum of the Raman scattered light is corrected so that a spatial frequency appearing in the spatial distribution of light intensities becomes uniform. In this way, it is possible to correct a distortion in the spatial distribution of light intensities of the spectrum of the Raman scattered light acquired by the spectroscope caused by an aberration of the spectroscope and thereby to acquire an accurate 2D image of the object to be observed.

A Raman scattered light observation method according to a fifteenth aspect of the present invention is the above-described Raman scattered light observation method, in which the spatial distribution of light intensities of the spectrum of the Raman scattered light is divided into a plurality of sections, a spatial frequency appearing in a spatial distribution of light intensities is acquired for each of the plurality of sections, a spatial pitch of the spatial distribution of light intensities for each of the plurality of sections is corrected so that a spatial frequency of each of the plurality of sections becomes equal to a reference value, and the spatial distribution of light intensities of the spectrum is corrected by combining the spatial-pitch-corrected spatial distributions of light intensities of the plurality of sections. In this way, it is possible to correct a spatial pitch of each section based on a spatial frequency of each section in a concrete manner.

A Raman scattered light observation method according to a sixteenth aspect of the present invention is the above-described Raman scattered light observation method, in which the light that is emitted from the light source and is incident on the diffraction device is collimated light. In this way, it is possible to prevent light having a large light intensity emitted from the light source used for the Raman spectroscopy from converging in the diffraction device and thereby to prevent the diffraction device from deteriorating.

A Raman scattered light observation method according to a seventeenth aspect of the present invention is the above-described Raman scattered light observation method, in which a phase and an intensity of 0th order diffracted light generated in the diffraction device are adjusted with respect to a phase of the +1st and −1st order diffracted lights, and the +1st and −1st order diffracted lights and the 0th order diffracted light are thereby made to interfere with each other so that interference fringes are formed in a depth direction of a sample. In this way, it is possible to form interference fringes in the depth direction of the sample and thereby to improve the spatial resolution in the depth direction of the sample.

A Raman scattered light observation method according to an eighteenth aspect of the present invention is the above-described Raman scattered light observation method, in which a beam cross-section converter is disposed on a light-source side of the diffraction device or on a side of the diffraction device opposite to the light-source side thereof, the beam cross-section converter being configured to change a shape of a beam cross-section of light passing therethrough. In this way, it is possible to make desired diffracted light incident on a pupil of an objective lens, through which illumination light is applied to a sample, even when the number of grooves in the diffraction device is fixed.

Advantageous Effects of Invention

According to the present invention, it is possible to achieve a spatial resolution that exceeds the diffraction limit of light in a Raman spectroscopic microscope.

DESCRIPTION OF EMBODIMENTS

Exemplary embodiments according to the present invention are explained hereinafter with reference to the drawings. The same symbols are assigned to the same components throughout the drawings, and their duplicated explanation is omitted as appropriate.

First Exemplary Embodiment

Figure 1:
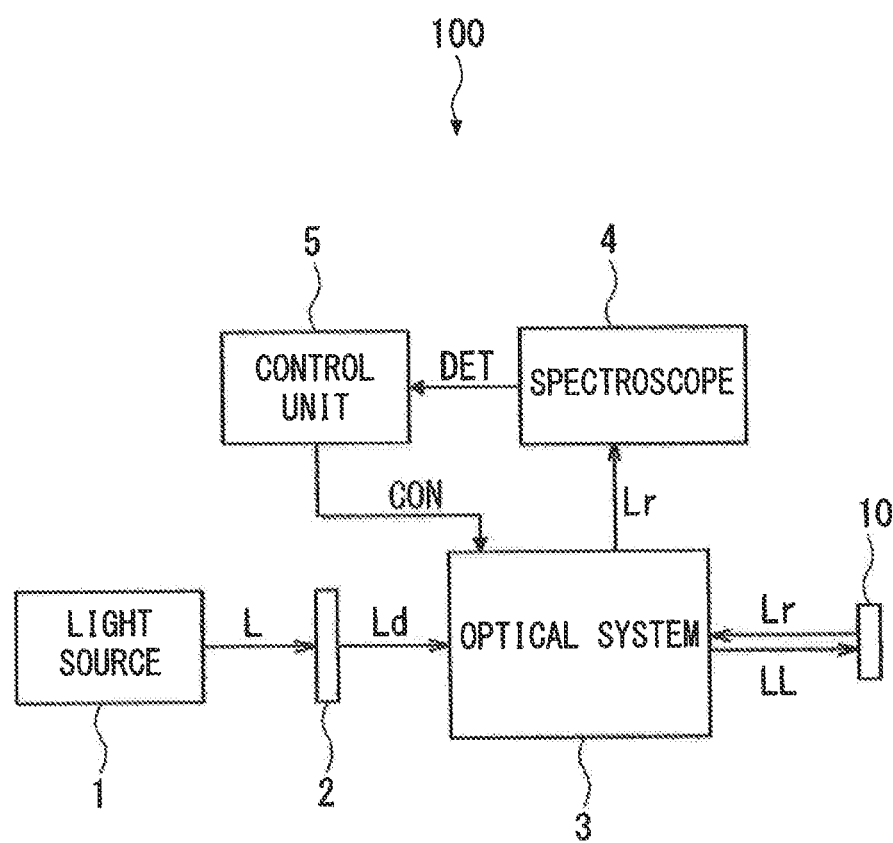
FIG. 1 is a block diagram schematically showing a fundamental configuration of a Raman spectroscopic microscope according to a first exemplary embodiment.
Figure 2:
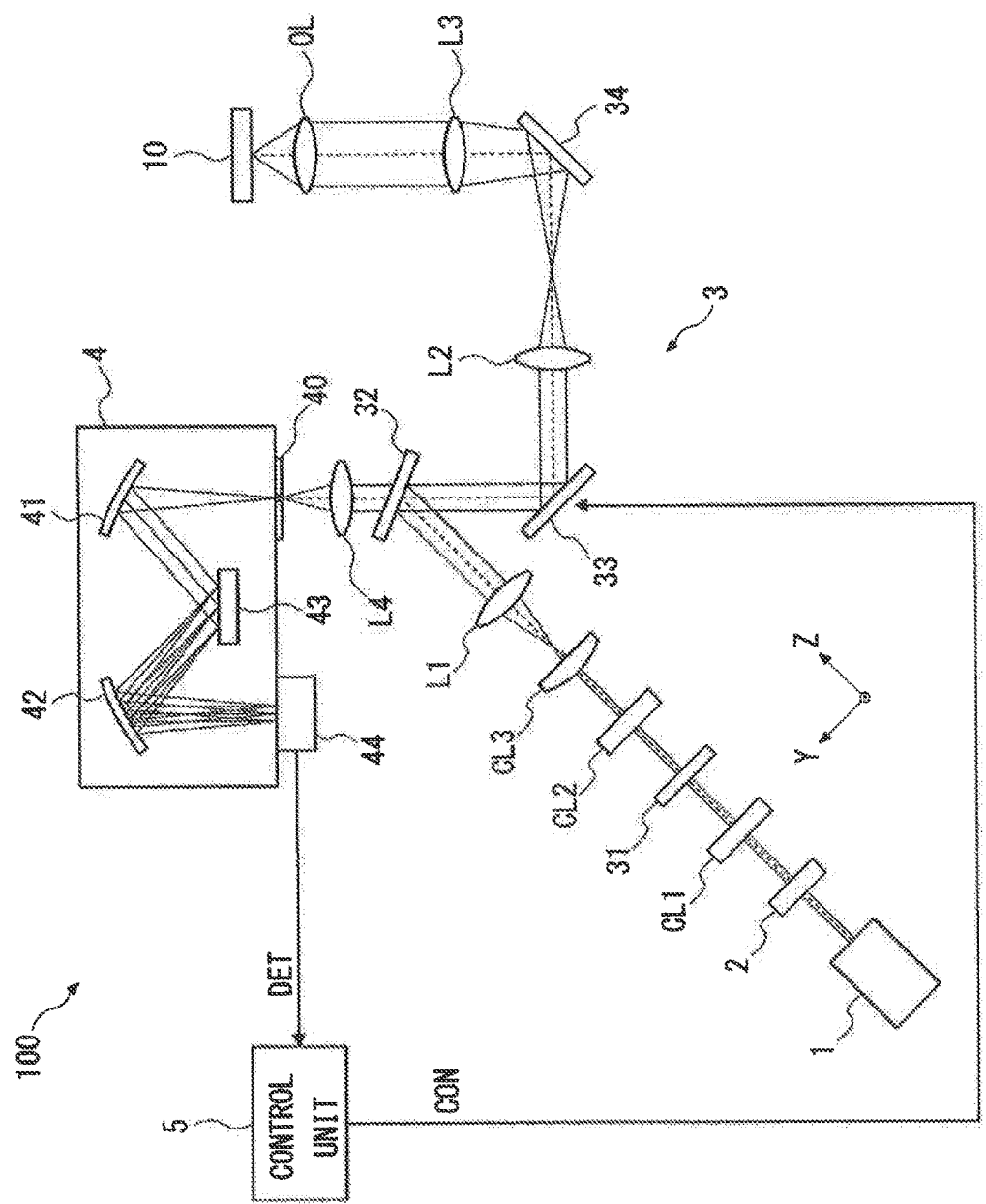
FIG. 2 is a top view schematically showing a configuration of the Raman spectroscopic microscope according to the first exemplary embodiment.
Figure 3:
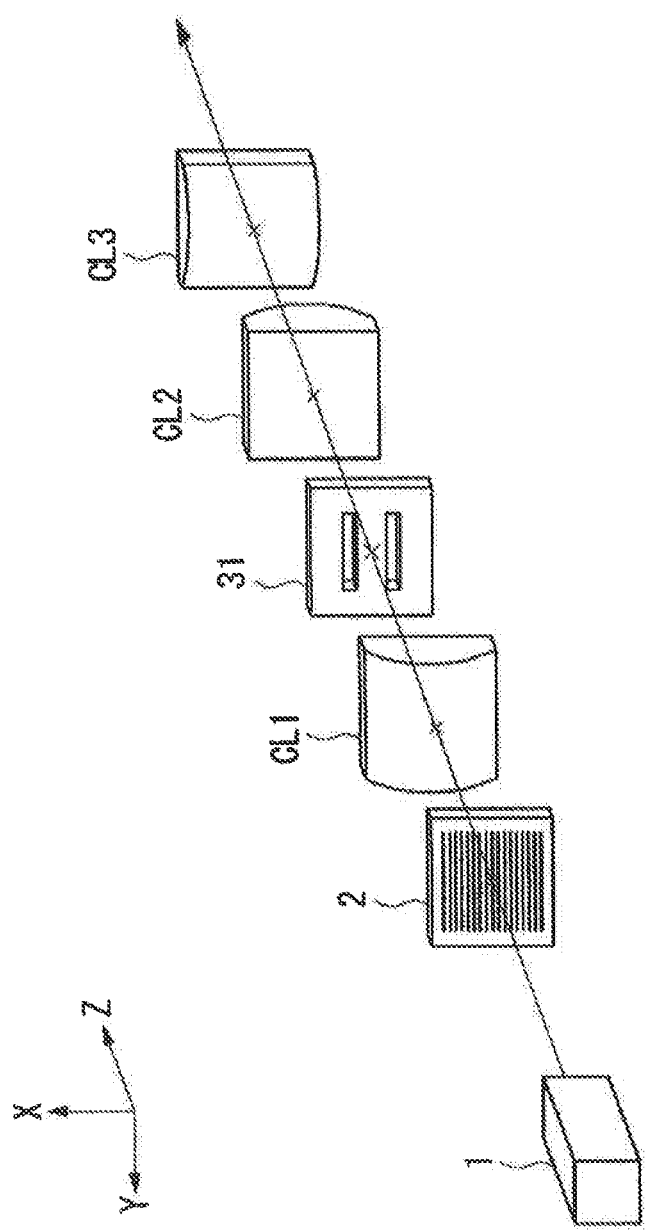
FIG. 3 is a perspective view of a configuration of a part of an optical system according to the first exemplary embodiment as viewed from a light-source side.

A Raman spectroscopic microscope according to a first exemplary embodiment is explained. FIG. 1 is a block diagram schematically showing a fundamental configuration of a Raman spectroscopic microscope 100 according to the first exemplary embodiment. FIG. 2 is a top view schematically showing a configuration of the Raman spectroscopic microscope 100 according to the first exemplary embodiment. FIG. 3 is a perspective view of a configuration of a part of an optical system 3 according to the first exemplary embodiment as viewed from a light source 1 side.

In FIGS. 1 to 3, the other figures, and the below explanation, a traveling direction of illumination light or Raman scattered light is defined as a Z-axis, irrespective of reflection of the light by a mirror and the like. Further, a direction perpendicular to the Z-axis is defined as an X-axis and a direction perpendicular to both the Z- and X-axes is defined as a Y-axis. In FIG. 2, the X-axis is a direction perpendicular to the surface of the paper. Further, the X- and Y-axis directions are also referred to as first and second directions, respectively.

The light source 1 is a monochrome light source. For example, a continuous-wave laser device is used as the light source 1. The light source 1 emits laser light L to a diffraction grating 2. Note that the laser light L is incident on the diffraction grating 2 as collimated light. In general, relatively high-power laser light is used in a Raman spectroscopic microscope. There is a possibility that when a high-power laser is made to converge in a diffraction grating, the diffraction grating could be damaged or deteriorated. Therefore, in this exemplary embodiment, the laser light L is incident on the diffraction grating 2 as collimated light, so that damage or deterioration of the diffraction grating can be prevented.

The diffraction grating 2 is a slit having its longitudinal direction in a direction in parallel with the Y-axis (i.e., a horizontal direction) or a diffraction device with a refractive-index distribution engraved thereon. In this way, diffracted light is generated. The following explanation is given while paying attention to 0th order diffracted light, +1st order diffracted light, and −1st order diffracted light. The 0th order diffracted light traveling in a straight line in the Z-axis direction, and the +1st and −1st order diffracted lights that are diffracted only by a predetermined angle on the X-Z plane are generated in the diffraction grating 2 and are incident on the optical system 3. The light including the 0th order diffracted light and the +1st and −1st order diffracted lights are expressed as illumination light Ld.

The optical system 3 guides the illumination light and applies it to an object to be observed 10 as linear illumination light LL (or line illumination light LL). Further, the optical system 3 guides Raman scattered light Lr that is generated by the application of the linear illumination light LL to the object to be observed 10 to a spectroscope 4. That is, the optical system 3 has both a function as an illumination optical system for guiding illumination light to an object to be observed and a function as an image-forming optical system for guiding Raman scattered light generated by the application of the illumination light to the object to be observed to the spectroscope.

The optical system 3 includes cylindrical lenses CL1 to CL3, lenses L1 to L4, an objective lens OL, a shield plate 31, an edge filter 32, a galvanometer mirror 33, and a mirror 34.

Figure 4:
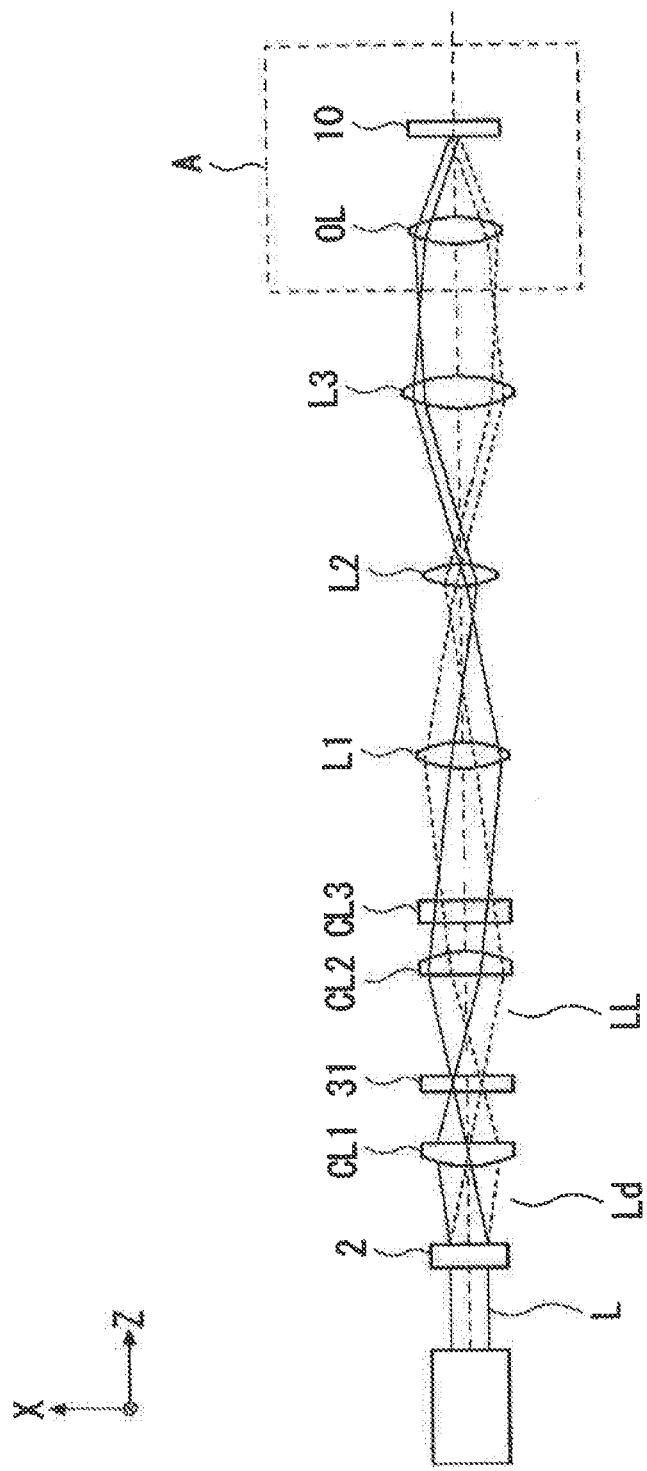
FIG. 4 is a side view schematically showing a configuration of an illumination optical system included in the optical system according to the first exemplary embodiment.

FIG. 4 is a side view schematically showing a configuration of an illumination optical system included in the optical system 3 according to the first exemplary embodiment. In FIG. 2, the optical path in the optical system 3 is bent. However, for easier understanding of the illumination optical system, the components of the illumination optical system are arranged in a straight line in FIG. 4. In FIG. 4, the +1st order diffracted light is indicated by solid lines and the −1st order diffracted light is indicated by short-chain lines. Further, the optical axis of the illumination light is indicated by a long-chain line. Further, the edge filter 32, the galvanometer mirror 33, and the mirror 34 are omitted in FIG. 4.

Firstly, the configuration of the optical system 3 is explained while paying attention to the illumination optical system.

The cylindrical lens CL1 is disposed in such a manner that its curved surface faces the diffraction grating 2 and refracts the optical path of the illumination light Ld on the X-Z plane. The illumination light Ld is shaped by the cylindrical lens CL1 so that it illuminates a belt-like area whose longitudinal direction is in parallel with the Y-axis.

The shield plate 31 blocks the 0th order diffracted light and ±2nd and higher order diffracted lights included in the illumination light Ld. The shield plate 31 has a slit having its longitudinal direction in the Y-axis direction that is configured so that the +1st and −1st order diffracted lights pass therethrough. Therefore, the shield plate 31 outputs linear illumination light LL including the +1st and −1st order diffracted lights.

The cylindrical lens CL2 is disposed in such a manner that its curved surface faces the cylindrical lens CL3 and refracts the optical path of the linear illumination light LL on the X-Z plane.

The cylindrical lens CL3 refracts the optical path of the linear illumination light LL that has passed through the cylindrical lens CL2 on the Y-Z plane.

The linear illumination light LL that is made to converge by the cylindrical lens CL3 and then diverges is incident on the lens L1. By the lens L1, the linear illumination light LL becomes collimated light on the Y-Z plane.

The linear illumination light LL that has passed through the lens L1 is reflected by the edge filter 32 and is incident on the lens L2. The linear illumination light LL that has passed through the lens L2 is reflected by the mirror 34 and is incident on the lens L3. The linear illumination light LL that has passed through the lens L3 becomes collimated light on the Y-Z plane and is incident on the objective lens OL.

Figure 5:
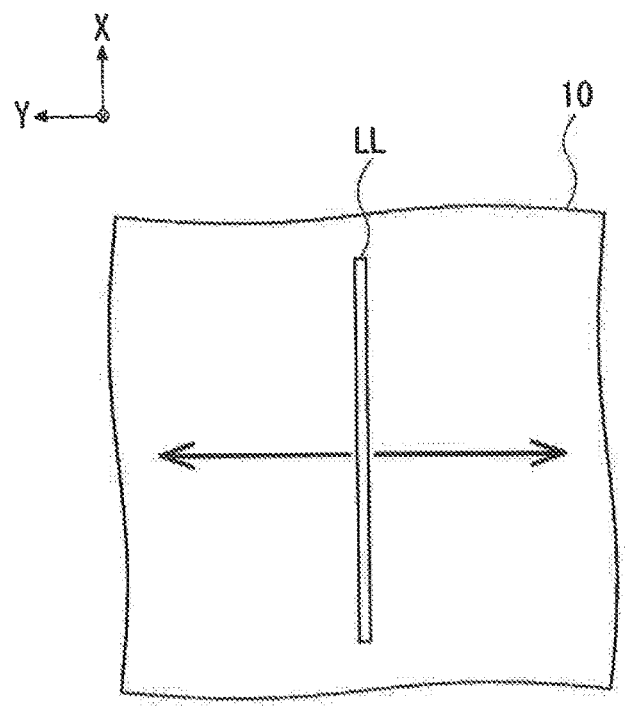
FIG. 5 is an enlarged view of a main part, schematically showing an irradiation place of linear illumination light on an object to be observed.

The objective lens OL concentrates the linear illumination light LL into a linear shape (or a line shape) on the object to be observed 10. FIG. 5 is an enlarged view of a main part, schematically showing an irradiation place of the linear illumination light LL on the object to be observed 10. As shown in FIG. 5, the linear illumination light LL is applied to an area whose longitudinal direction is in the vertical direction (i.e., the X-axis direction) on the object to be observed 10.

Figure 6:
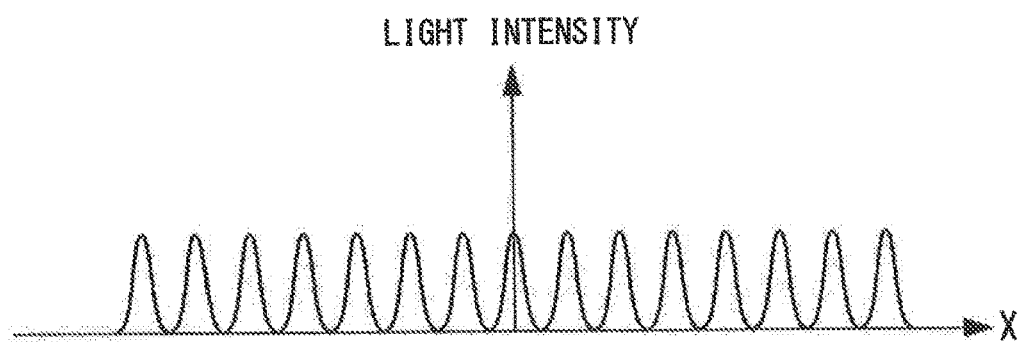
FIG. 6 schematically shows an intensity distribution of linear illumination light on an object to be observed.

In the linear illumination light LL which is formed into an image on the object to be observed 10, interference fringes in which light parts and dark parts reiterate in the X-axis direction appear since the +1st interference light and −1st interference light interfere with each other. FIG. 6 schematically shows an intensity distribution of the linear illumination light LL on the object to be observed 10. As shown in FIG. 6, interference fringes in which successive sharp peaks reiterate in the X-axis direction appear in the linear illumination light. That is, the linear illumination light LL is applied to the object to be observed 10 as structured illumination light having a light intensity distribution resulting from the interference fringes.

By illuminating a sample by an illumination pattern having a fine structure close to the diffraction limit, it is possible to shift the spatial frequency of information that appears as a formed image and thereby to form an image having a spatial frequency that exceeds the diffraction limit on a light-receiving surface.

Figure 7:
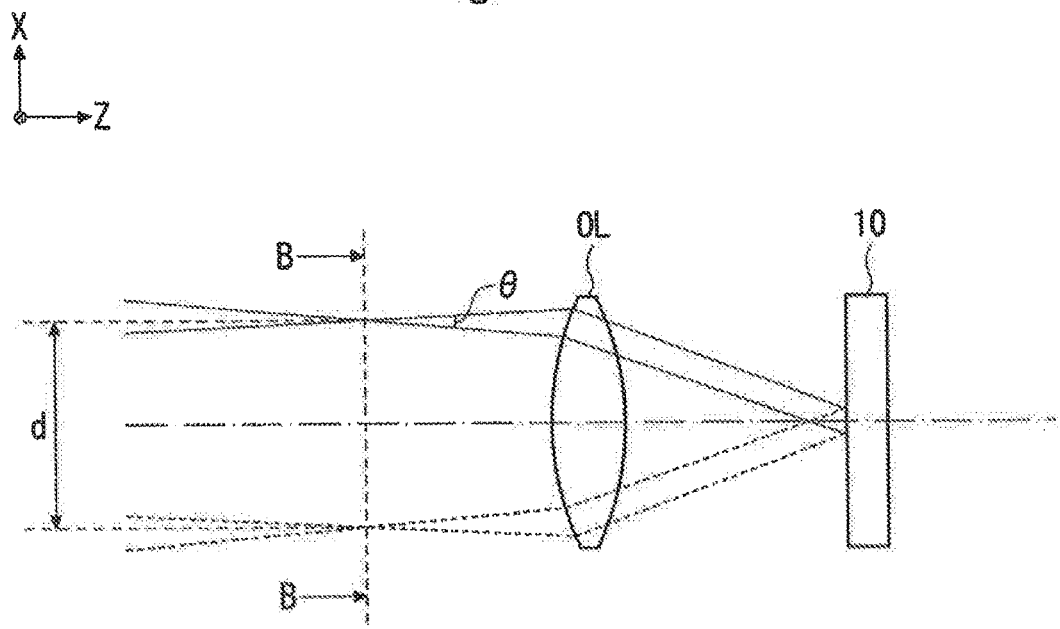
FIG. 7 is an enlarged view of an area A including an objective lens and an object to be observed shown in FIG. 4.
Figure 8:
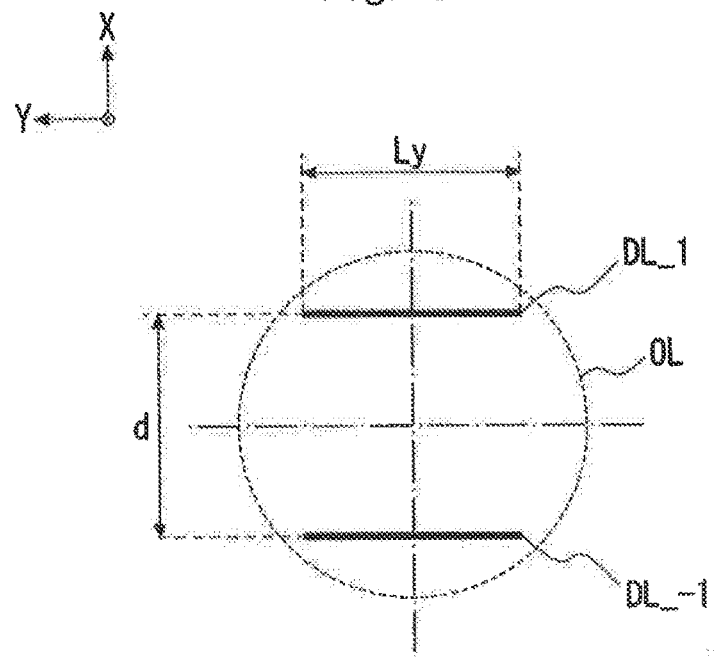
FIG. 8 shows an example in which diffracted light in a light-concentrating place (line B-B in FIG. 7) thereof located before an objective lens is observed from a light-source side.

FIG. 7 is an enlarged view of an area A including the objective lens OL and the object to be observed 10 shown in FIG. 4. FIG. 8 shows an example in which diffracted light in a light-concentrating place (a line B-B in FIG. 7) thereof located before the objective lens OL (i.e., located on the incident side of the objective lens OL) is observed from a light-source side. In this exemplary embodiment, it is necessary to adjust a length Ly of two lines formed by diffracted light (symbols DL1_1 and DL_-1 in FIG. 8) in the light-concentrating place (the line B-B) thereof, an interval d between the two lines, and a convergence angle θ between the two lines to appropriate vales. The length Ly of the two lines determines a numerical aperture (NA) of the structured illumination light. The interval d of the two lines determines a pitch of interference fringes appearing in the linear illumination light LL. The convergence angle θ between the two lines determines a length of the linear illumination light.

The length, the interval, and the convergence angle of the two lines formed in the pupil of the objective lens OL by the diffracted light can be determined by the diffraction grating 2. However, in general, the number of grooves in a commercially-available diffraction grating is a discrete number such as 300, 600 and 1,200. Therefore, it is necessary to design a dedicated diffraction grating according to an objective lens to be used in order to obtain a diffraction grating optimally suited for the above-described optical system. Consequently, a large expenditure is required to obtain the diffraction grating.

In contrast to this, in this exemplary embodiment, the two cylindrical lenses CL1 and CL2 having focal lengths different from each other are inserted behind the diffraction grating 2 (i.e., inserted on the output side of the diffraction grating 2). Further, the cylindrical lenses CL2 and CL3 are disposed in such a manner that they are rotated relative to each other around the optical axis (i.e., the Z-axis) by 90°. In this way, the cylindrical lenses CL1 and CL2, which serve as a beam cross-section converter, can expand or contract the beam cross section of light passing therethrough, and convert the shape of the beam cross section into an ellipse. As a result, it is possible to optimize the length, the interval, and the convergence angle of the two lines formed in the pupil of the objective lens OL by the diffracted light by the cylindrical lenses CL2 and CL3 even when the number of grooves in the diffraction grating 2 is fixed. Note that although the beam cross-section converter is disposed behind the diffraction grating 2 in the above-described example, the beam cross-section converter may be disposed between the light source 1 and the diffraction grating 2. Note that the beam cross-section converter can be formed by using a pair of anamorphic prisms, instead of using the above-described pair of cylindrical lenses.

Next, the configuration of the optical system 3 is explained while paying attention to the image-forming optical system.

The Raman scattered light Lr generated in the object to be observed 10 is incident on the objective lens OL. The Raman scattered light Lr reaches the edge filter 32 through a route the reverse of the route of the linear illumination light LL, i.e., through the objective lens OL, the lens L3, the mirror 34, the lens L2, and the galvanometer mirror 33.

The edge filter 32 is designed so as to let the Raman scattered light Lr pass therethrough. The Raman scattered light Lr, which has passed through the edge filter 32, is made to converge by the lens L4 and is incident on the spectroscope 4.

The spectroscope 4 spectroscopically analyzes the Raman scattered light Lr. The spectroscope 4 includes a slit 40, concave mirrors 41 and 42, a dispersive device 43, and a detection unit 44. The Raman scattered light Lr incident on the slit 40 of the spectroscope 4 is converted into collimated light by the concave mirror 41 and is incident on the dispersive device 43.

As the dispersive device 43, for example, a diffraction grating, a prism, or the like can be used. The dispersive device 43 spectrally disperses the Raman scattered light Lr and outputs the spectrally-dispersed light to the concave mirror 42. The concave mirror 42 makes the spectrally-dispersed light converge so that it forms an image in the detection unit 44.

The detection unit 44 includes, for example, an image pickup device (such as a CCD (Charge Coupled Device) image sensor, a CMOS (Complementary Metal Oxide Semiconductor) image sensor, or the like) that detects the spectrally-dispersed Raman scattered light Lr. On this image pickup device, the spectrally-dispersed Raman scattered light having different wavelengths is spatially separated and forms an image. Therefore, it is possible to obtain a spectrum of the Raman scattered light Lr by performing an image-shooting by using the image pickup device. Note that since the X-axis direction of the shot image corresponds to the longitudinal direction of the linear illumination, spatial information (i.e., a light intensity distribution) in the vertical direction (i.e., the X-axis direction) of the object to be observed 10 is obtained. Meanwhile, the spectrum of the Raman scattered light is distributed in the Y-axis direction. The spectroscope 4 can output a result of the spectroscopy (i.e., spectrums and a light intensity distribution for each spectrum) to a control unit 5 as a signal DET.

The control unit 5 controls an operation of the Raman spectroscopic microscope 100. Specifically, it is possible to scan the object to be observed 10 in the Y-axis direction (indicated by an arrow in FIG. 5) by the linear illumination light LL by controlling the movement of the galvanometer mirror 33 of the optical system 3 by using a control signal CON.

Next, an operation of the Raman spectroscopic microscope 100 is explained.

The Raman spectroscopic microscope 100 applies (i.e., emits) linear illumination light LL to the object to be observed 10. As described above, it is possible to obtain a light intensity distribution in the X-axis direction of the Raman scattered light Lr coming from an area of the object to be observed 10 to which the linear illumination light LL is applied based on the spectroscopic result obtained in the spectroscope 4.

Further, as indicated by the arrow in FIG. 5, the Raman spectroscopic microscope 100 scans the object to be observed 10 in the Y-axis direction by the linear illumination light LL. In this way, it is possible to acquire a light intensity distribution in the Y-axis direction of the object to be observed 10.

As explained above, it is possible to acquire a 2D light intensity distribution of Raman scattered light on the X-Y plane of the object to be observed by combining linear illumination in which structured illumination is introduced and a scanning operation. In this way, the Raman spectroscopic microscope 100 can acquire a 2D image of the object to be observed.

In the Raman spectroscopic microscope 100, it is desirable that the resolution in the Y-axis direction be equal to the resolution in the X-axis direction in the 2D image of the object to be observed 10. In the Raman spectroscopic microscope 100, the trade-off relation between the resolutions in the X- and Y-axis directions is determined by the diffraction angle of the incident light in the diffraction grating 2. It is possible to control the scanning speed or the scanning pitch in the Y-axis direction of the linear illumination light by controlling the rotation speed or the rotation pitch of the galvanometer mirror 33 by using the control unit 5. That is, it is possible to make the resolutions in the X- and Y-axis directions equal to each other in the 2D image of the object to be observed 10 by appropriately selecting the number of grooves in the diffraction grating 2 and having the control unit 5 control the scanning speed or the scanning pitch so that the resolutions in the X- and Y-axis directions become equal to each other.

Further, in the Raman spectroscopic microscope 100, it is possible to change the phase of the interference fringes of the linear illumination light LL in a multi-step manner (e.g., in three steps) by making the diffraction grating 2 movable on the X-axis by using a piezo-actuator or the like and driving (i.e., moving) its position by using the control unit 5. In this way, by changing the phase, it is possible to change the interference fringes in a range smaller than the interval of the interference fringes. Further, by performing a Fourier transform on a spatial distribution of light intensities of a plurality of spectrums, each of which is obtained for a respective one of the phases of the changed interference fringes for each wavelength, combining them in a frequency space, and then performing an inverse Fourier transform, it is possible to generate a spatial distribution of light intensities of the spectrums in the irradiation place. In this way, it is possible to improve the spatial resolution in the X-axis direction of the object to be observed compared to that of an ordinary slit confocal Raman spectroscopic microscope.

Example 1

Figure 9:
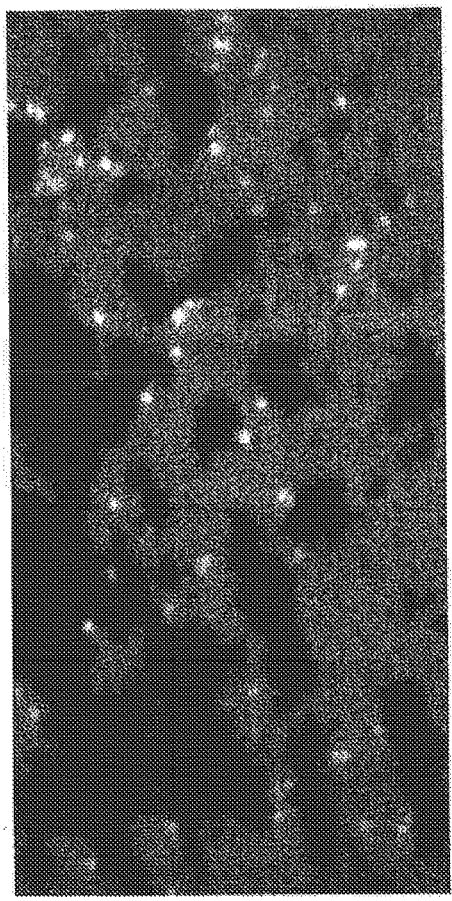
FIG. 9 shows an observed image of a sample in a Raman spectroscopic microscope according to the first exemplary embodiment (Example 1) and that in an ordinary Raman spectroscopic microscope, which is used as a comparative example (Comparative Example 1)
Figure 9:
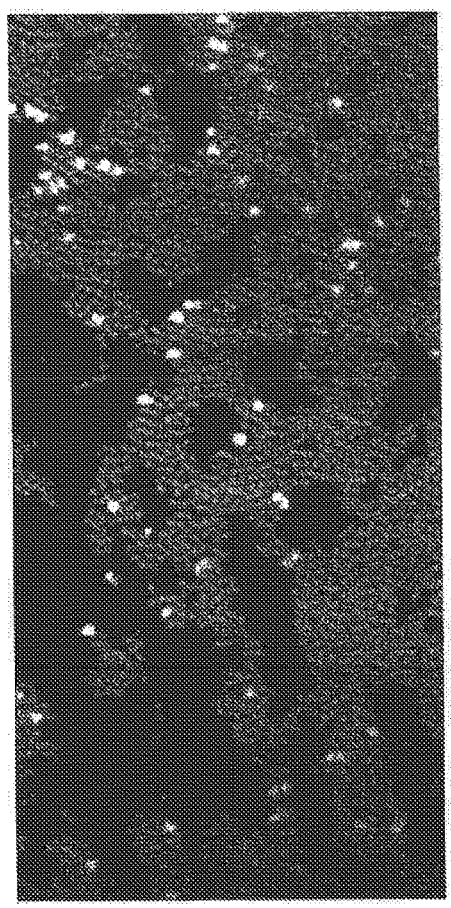

FIG. 9 shows an observed image of a sample in the Raman spectroscopic microscope 100 according to the first exemplary embodiment (Example 1) and that in an ordinary Raman spectroscopic microscope, which is used as a comparative example (Comparative Example 1). FIG. 9 shows Raman images (1,003 cm$^{-1}$) of polystyrene microspheres having a diameter of 500 nm. In the comparative example, a slit confocal Raman spectroscopic microscope using no structured illumination was used. As can be seen from FIG. 9, it can be confirmed that the Raman spectroscopic microscope 100 can obtain an image of polystyrene microspheres at a higher resolution than that of the ordinary slit confocal Raman spectroscopic microscope.

Example 2

Figure 10:
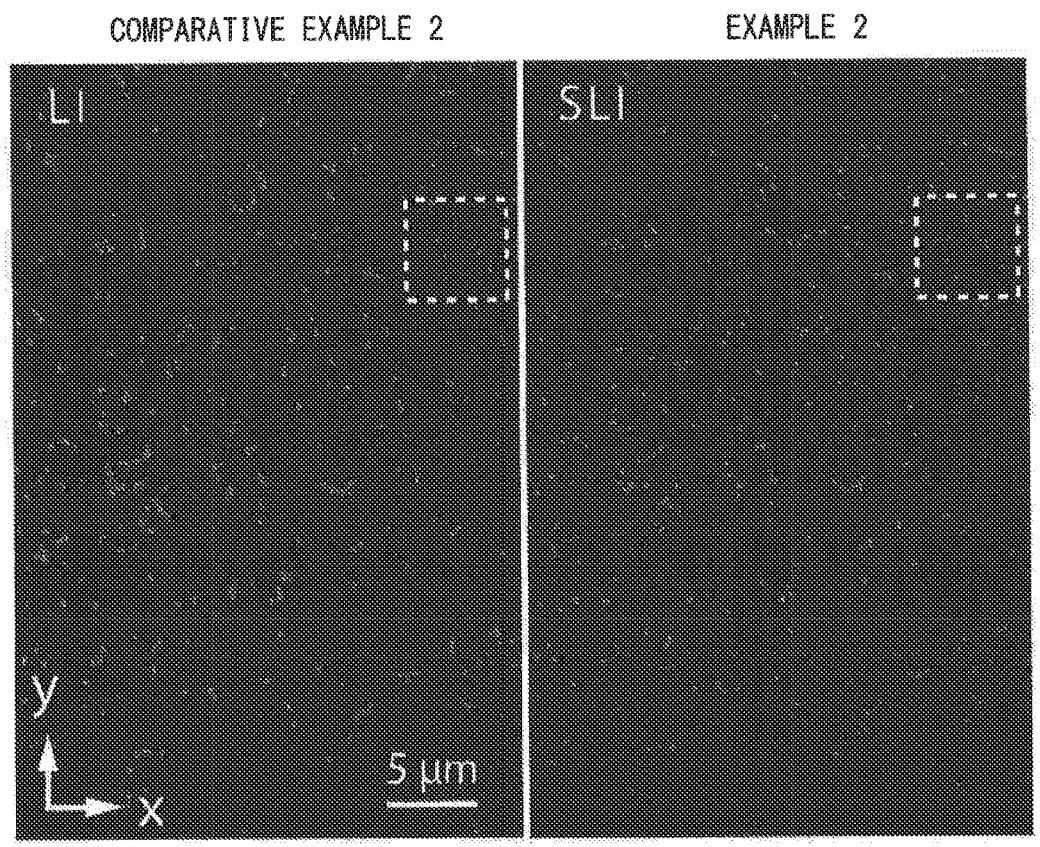
FIG. 10 shows an observed image of a sample in a Raman spectroscopic microscope according to the first exemplary embodiment (Example 2) and that in an ordinary Raman spectroscopic microscope, which is used as a comparative example (Comparative Example 2)

FIG. 10 shows an observed image of a sample in the Raman spectroscopic microscope 100 according to the first exemplary embodiment (Example 2) and that in an ordinary Raman spectroscopic microscope, which is used as a comparative example (Comparative Example 2). FIG. 10 shows Raman images of mixed microspheres of polystyrene and polymethyl methacrylate (PMMA) having diameters of 500 to 800 nm on a glass substrate at wavenumbers of 3,055 cm$^{-1}$ and 2,957 cm$^{-1}$. In Comparative Example 2, a slit confocal Raman spectroscopic microscope using no structured illumination was used. In FIG. 10, light-shaded microspheres are polystyrene microspheres and dark-shaded microspheres are PMMA microspheres. As can be seen from FIG. 10, it can be confirmed that the Raman spectroscopic microscope 100 can obtain an image of microspheres at a higher resolution than that of the ordinary slit confocal Raman spectroscopic microscope.

Figure 11:
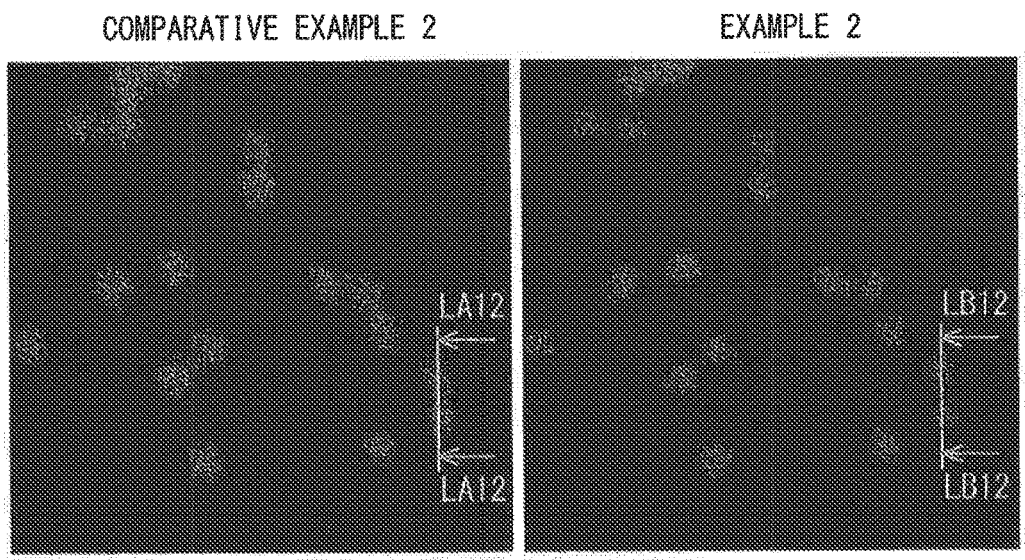
FIG. 11 is an enlarged view of an area surrounded by a broken line in FIG. 10.
Figure 12:
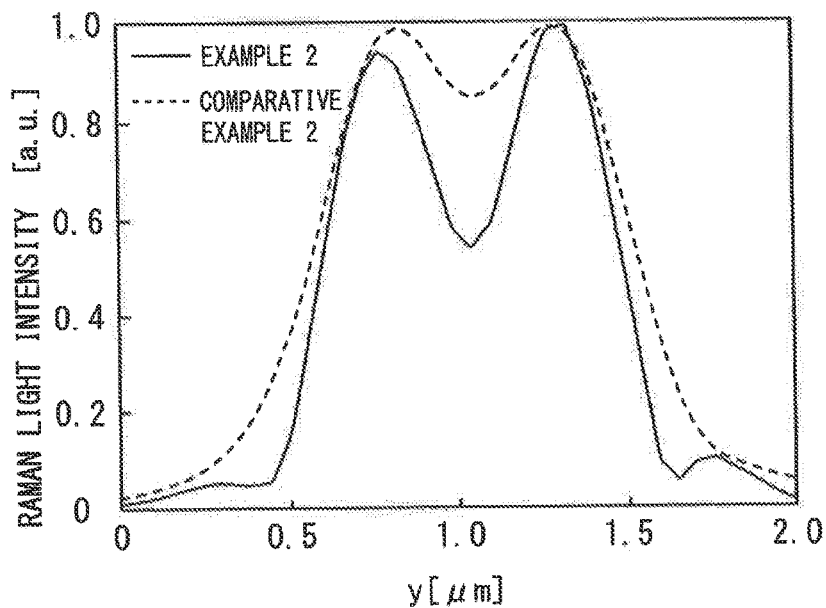
FIG. 12 shows Raman light intensities at a wavenumber of 3,055 $cm^{-1}$ on a line LA12-LA12 in FIG. 11 (Comparative Example 2) and those on a line LB12-LB12 in FIG. 11 (Example 2)

FIG. 11 is an enlarged view of an area surrounded by a broken line in FIG. 10. FIG. 12 shows Raman light intensities at a wavenumber of 3,055 cm$^{-1}$ on a line LA12-LA12 in FIG. 11 (Comparative Example 2) and those on a line LB12-LB12 in FIG. 11 (Example 2). In FIG. 12, Example 2 is indicated by a solid line and Comparative Example 2 is indicated by a broken line. Here, attention is paid to two microspheres. As shown in FIG. 12, two peaks corresponding to the two microspheres overlap each other in Comparative Example 2. In contrast to this, it can be confirmed that the gap between the two spheres are clearly shown in Example 2. That is, according to the Raman spectroscopic microscope 100 in accordance with the first exemplary embodiment, it can be understood that the spatial resolution in the observation of a micro-structure can be improved compared to that of the ordinary Raman spectroscopic microscope.

Example 3

Figure 13:
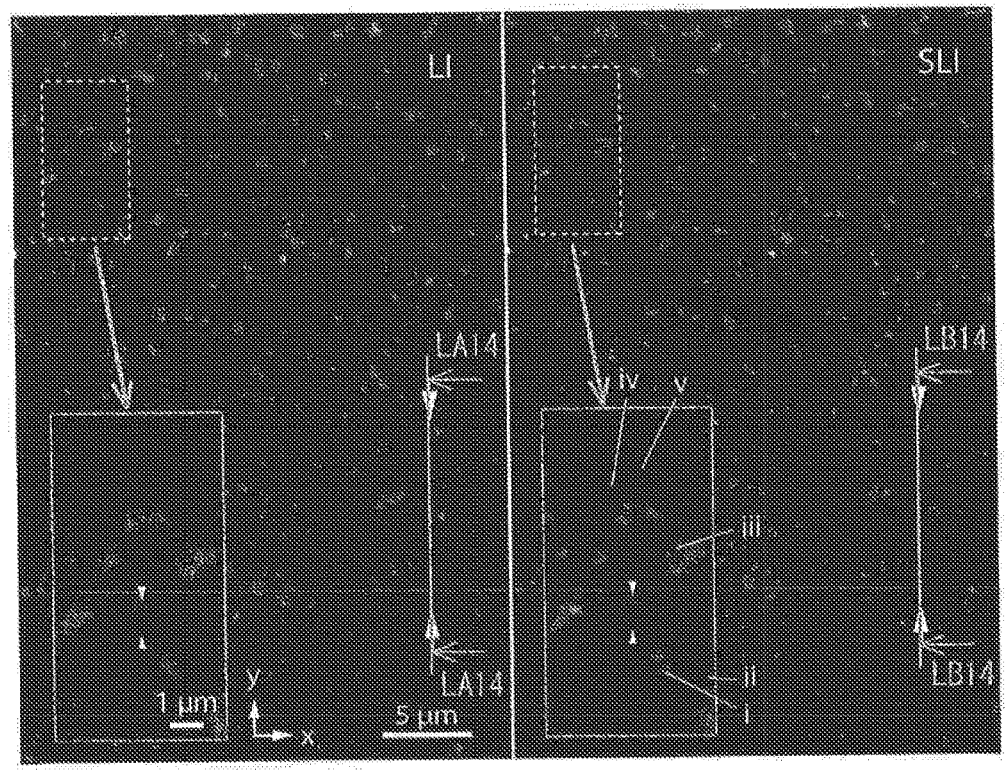
FIG. 13 shows an observed image of a sample in a Raman spectroscopic microscope according to the first exemplary embodiment (Example 3) and that in an ordinary Raman spectroscopic microscope, which is used as a comparative example (Comparative Example 3)

FIG. 13 shows an observed image of a sample in the Raman spectroscopic microscope 100 according to the first exemplary embodiment (Example 3) and that in an ordinary Raman spectroscopic microscope, which is used as a comparative example (Comparative Example 3). FIG. 13 shows single-layer graphene, two-layer graphene, graphite, and a defect formed therein. In Comparative Example 3, a slit confocal Raman spectroscopic microscope using no structured illumination was used. As can be seen from FIG. 13, it can be confirmed that the Raman spectroscopic microscope 100 can obtain the micro-structure of the sample at a higher resolution than that of the ordinary slit confocal Raman spectroscopic microscope. Note that in FIG. 13, symbols i, ii, iii, iv, and v indicate the graphite, the defect, lamination of the single-layer graphene, the two-layer graphene, and the single-layer graphene, respectively.

Figure 14:
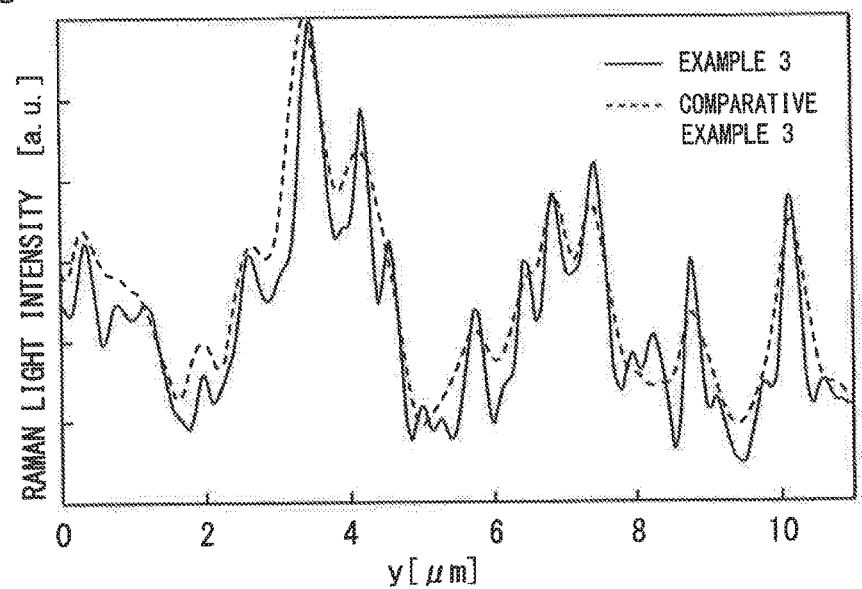
FIG. 14 shows average Raman light intensities in a range of wavenumbers from 1,307 to 1,387 $cm^{-1}$ (D-band) on a line LA14-LA14 in FIG. 13 (Comparative Example 3) and those on a line LB14-LB14 in FIG. 13 (Example 3)

FIG. 14 shows average Raman light intensities in a range of wavenumbers from 1,307 to 1,387 $cm^{-1}$ (D-band) on a line LA14-LA14 in FIG. 13 (Comparative Example 3) and those on a line LB14-LB14 in FIG. 13 (Example 3). In FIG. 14, Example 3 is indicated by a solid line and Comparative Example 3 is indicated by a broken line. As shown in FIG. 14, the Raman spectroscopic microscope 100 according to the first exemplary embodiment has a spatial frequency higher than that of an ordinary Raman spectroscopic microscope, that is, has a higher spatial resolution than that of the ordinary Raman spectroscopic microscope.

Example 4

Figure 15:
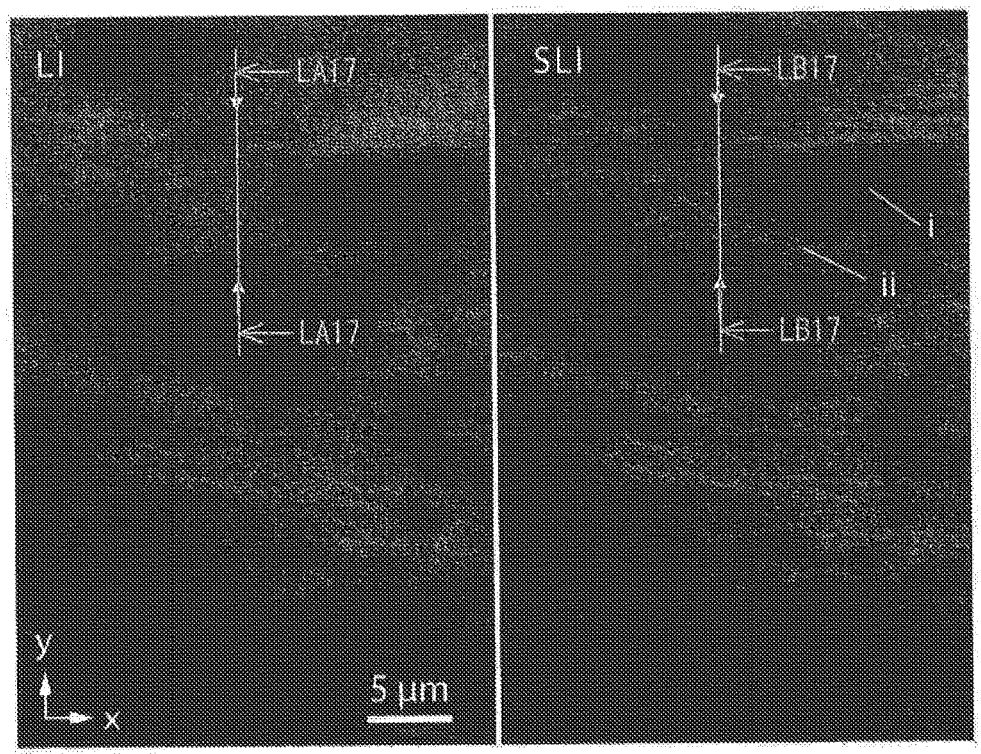
FIG. 15 shows an observed image of a sample in a Raman spectroscopic microscope according to the first exemplary embodiment (Example 4) and that in an ordinary Raman spectroscopic microscope, which is used as a comparative example (Comparative Example 4)

FIG. 15 shows an observed image of a sample in the Raman spectroscopic microscope 100 according to the first exemplary embodiment (Example 4) and that in an ordinary Raman spectroscopic microscope, which is used as a comparative example (Comparative Example 4). FIG. 15 shows Raman images of a specimen that is produced by slicing a cerebral tissue of a test mouse. In Comparative Example 4, a slit confocal Raman spectroscopic microscope using no structured illumination was used. In these examples, observed images at a wavenumber of 1,682 $cm^{-1}$ (corresponding to an amid I band (C=O expansion/contraction), red) and a wavenumber of 2,828 $cm^{-1}$ (corresponding to expansion/contraction of a $CH_2$ group, green) are shown in order to observe β sheets and lipid of proteins. As can be seen from FIG. 15, it can be confirmed that the Raman spectroscopic microscope 100 can obtain an image of the structure of the specimen at a higher resolution than that of the ordinary slit confocal Raman spectroscopic microscope.

Figure 16:
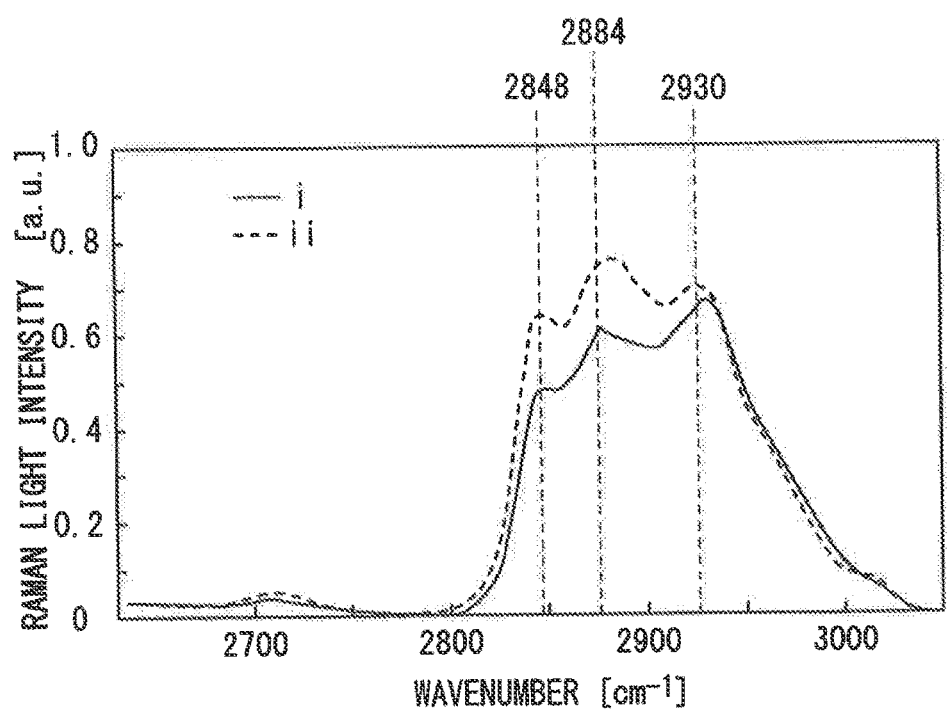
FIG. 16 shows spectrums of Raman light at points i and ii in FIG. 15.

FIG. 16 shows spectrums of Raman light at points i and ii in FIG. 15. As shown in FIG. 16, it can be understood that peaks corresponding to expansion/contraction of a CH group (a hydrocarbon group) (i.e., peaks at 2,848 $cm^{-1}$, 2,884 $cm^{-1}$ and 2,930 $cm^{-1}$) appear.

Figure 17:
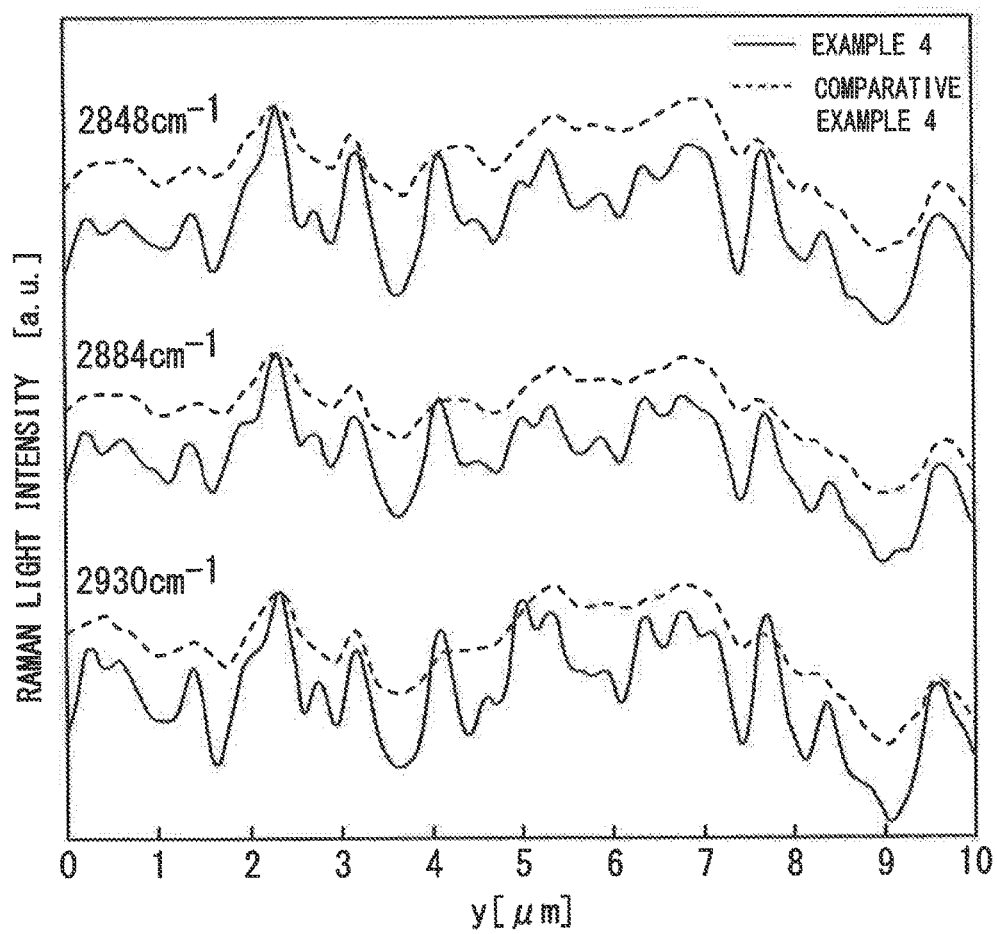
FIG. 17 shows intensity distributions of Raman light at peaks (2,848 cm$^{-1}$, 2,884 cm$^{-1}$ and 2,930 cm$^{-1}$) corresponding to expansion/contraction of a CH group (a hydrocarbon group) in Comparative Example 4 (a line LA17-LA17 in FIG. 15) and those in Example 4 (a line LB17-LB17 in FIG. 15)

FIG. 17 shows intensity distributions of Raman light at peaks (2,848 $cm^{-1}$, 2,884 $cm^{-1}$, and 2,930 $cm^{-1}$) corresponding to expansion/contraction of a CH group (a hydrocarbon group) in Comparative Example 4 (a line LA17-LA17 in FIG. 15) and those in Example 4 (a line LB17-LB17 in FIG. 15). In FIG. 17, Example 4 is indicated by a solid line and Comparative Example 4 is indicated by a broken line. As shown in FIG. 17, it can be understood that Example 4 enables the micro-structure of the specimen to be observed in a more detailed manner compared to Comparative Example 4. That is, the Raman spectroscopic microscope 100 according to the first exemplary embodiment makes it possible to observe specimens of living bodies as well as inorganic samples shown in Examples 1 to 3 with excellent resolutions.

From the above-described examples, it can be understood that the Raman spectroscopic microscope 100 according to the first exemplary embodiment can improve the spatial resolution in the observation of a micro-structure compared to the ordinary Raman spectroscopic microscope irrespective of the form of samples.

Second Exemplary Embodiment

A Raman spectroscopic microscope 200 according to a second exemplary embodiment is explained. The Raman spectroscopic microscope 200 differs from the Raman spectroscopic microscope 100 in that the control unit 5 of the Raman spectroscopic microscope 200 performs an operation for correcting a distortion in a light intensity distribution caused by an aberration of the spectroscope. Note that the configuration of the Raman spectroscopic microscope 200 is similar to that of the Raman spectroscopic microscope 100 and therefore its explanation is omitted.

Figure 18:
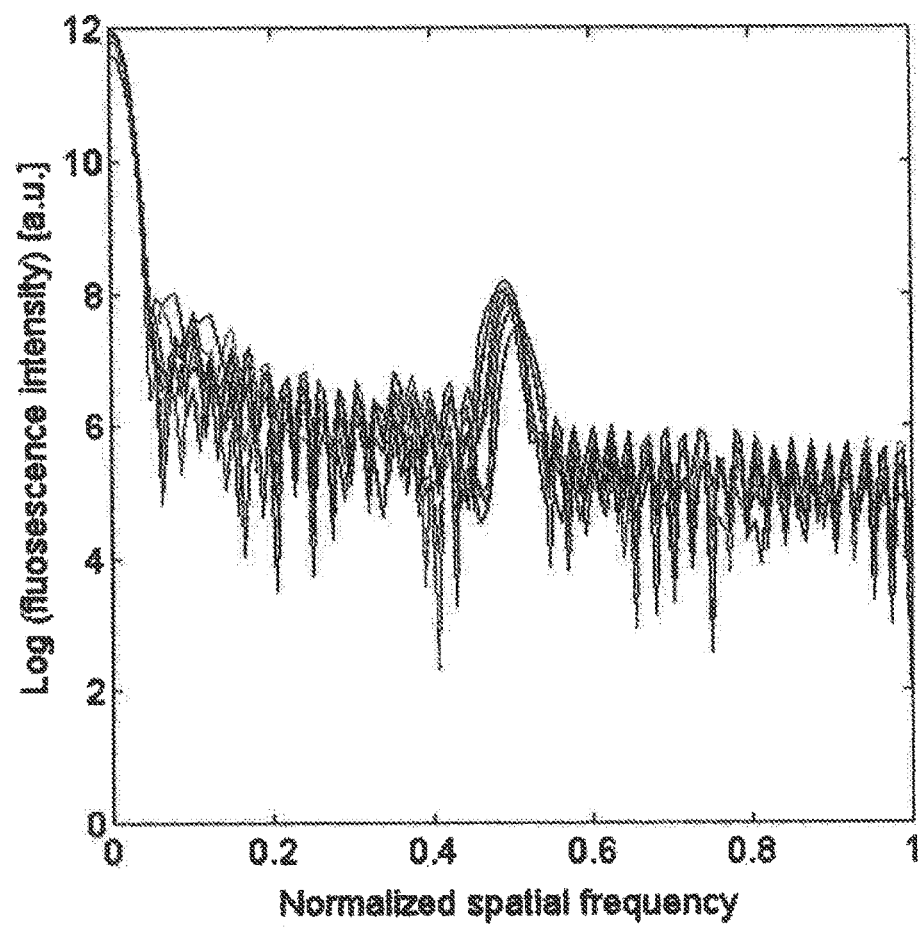
FIG. 18 is a graph showing deviations of measured spatial frequencies of interference fringes.

In general, the spectroscope 4 has an aberration. Therefore, a distortion occurs in a light intensity distribution due to the aberration during a process in which Raman scattered light Lr incident on the slit 40 is spectrally-dispersed and reaches the detection unit 44. FIG. 18 is a graph showing deviations of measured spatial frequencies of interference fringes. The horizontal axis in FIG. 18 indicates spatial frequencies in the longitudinal direction of the linear illumination light (i.e., in the direction in parallel with the X-axis). The vertical axis in FIG. 18 indicates a light intensity distribution of spectrally-dispersed Raman scattered light. Further, there are a plurality of lines representing light intensity distributions. They represent light intensity distributions for different observation places in the X-axis direction.

Figure 19:
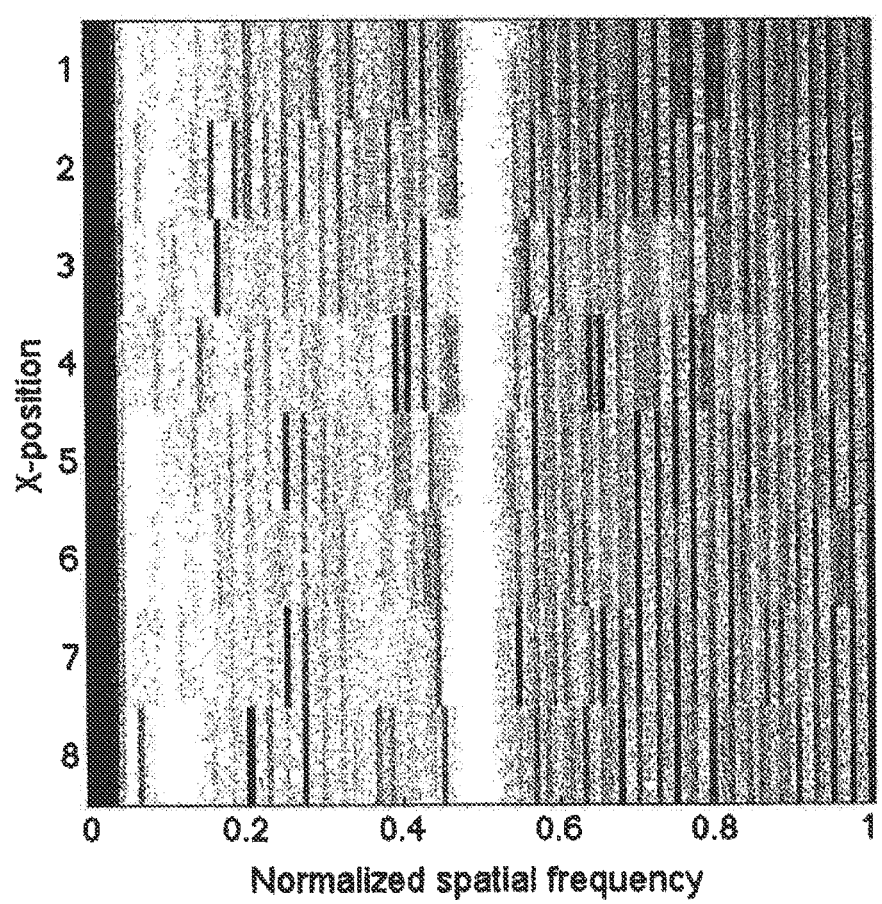
FIG. 19 shows a relation between deviations of spatial frequencies of interference fringes shown in FIG. 18 and their places on an X-axis.

FIG. 19 shows a relation between the deviations of spatial frequencies of interference fringes shown in FIG. 18 and their places on the X-axis. In FIG. 19, it can be confirmed that a part having a strong light intensity (i.e., a light pattern part) present at or near a normalized spatial frequency of 0.5 shifts to the negative side as the value indicating the observation place in the X-axis direction increases. Note that the horizontal axis in FIG. 19 indicates normalized spatial frequencies.

In the Raman spectroscopic microscope 100, it can be confirmed that since the structured illumination is used for the linear illumination light, variations in the light intensities in the X-axis direction of the linear illumination light, i.e., the spatial frequencies appear in the light intensity distribution as shown in FIG. 18. Note that since the spatial frequency appearing in the light intensity distribution is determined by the interference of the diffracted lights generated in the diffraction grating 2, the spatial frequency is, in principle, constant irrespective of the place on the X-axis. However, when the spectroscope has an aberration, the light intensity distribution is distorted. Therefore, variations occur in the spatial frequency appearing in the light intensity distribution. As a result, the 2D light intensity distribution shown in FIG. 19 is distorted, thus making the acquisition of an accurate image of the object to be observed impossible.

Figure 20:
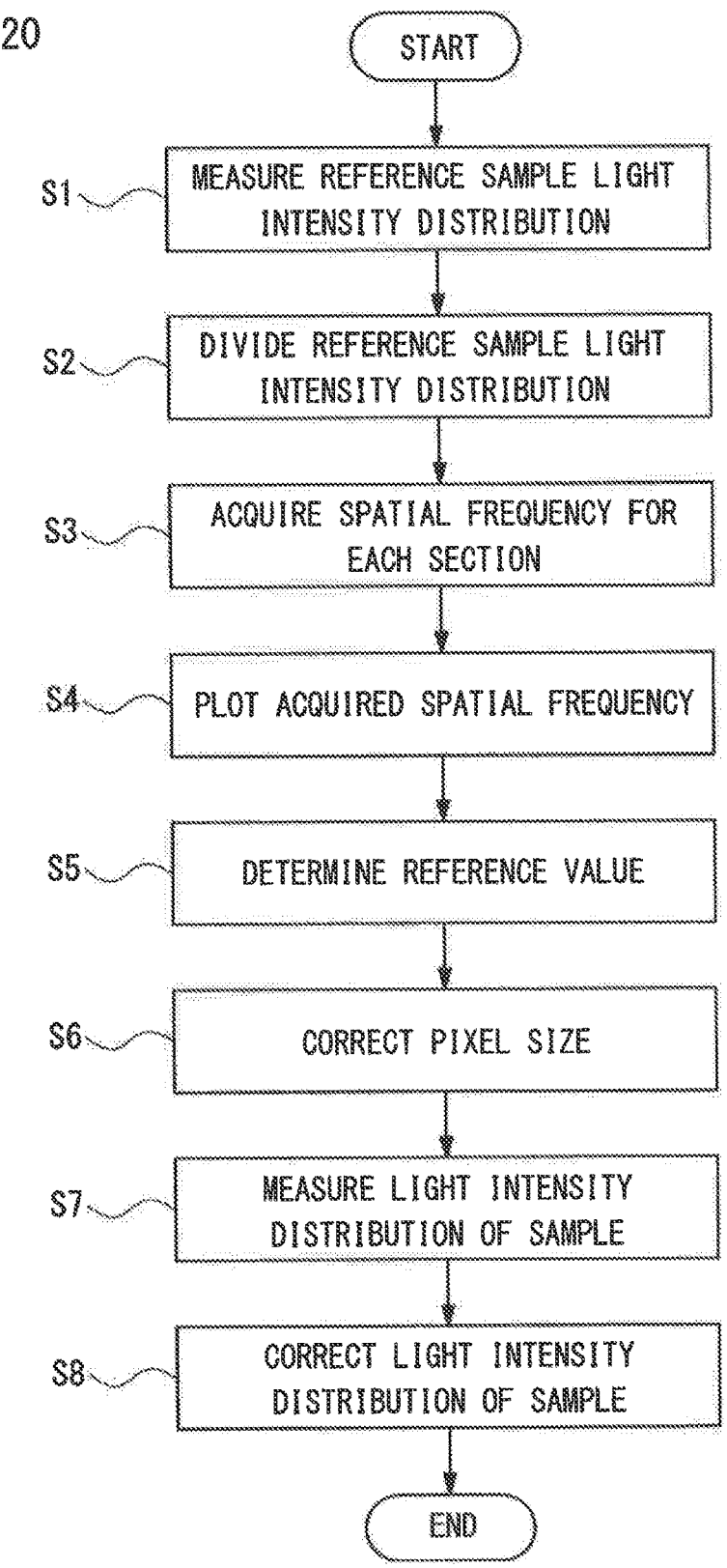
FIG. 20 is a flowchart showing an operation for correcting a distortion in a light intensity distribution of a Raman spectroscopic microscope image according to a second exemplary embodiment.

In contrast to this, the Raman spectroscopic microscope 200 has a function of acquiring an accurate image of the object to be observed by correcting a distortion in the light intensity distribution caused by the spectroscope 4 and caused in the optical path from the light source 1 to the spectroscope 4 (in particular, a curvature aberration). The spectroscope is indispensable to the Raman spectroscopic microscope. However, the aberration caused by the spectroscope is larger than the aberration caused in the optical path from the light source to the spectroscope. Therefore, if the aberration caused by the spectroscope cannot be corrected, it is impossible to acquire an accurate image of the object to be observed. This means that a correction of a distortion in the light intensity distribution explained below is meaningful particularly for the Raman spectroscopic microscope. A correcting operation performed in the Raman spectroscopic microscope 200 is explained hereinafter. Note that the below-explained correcting operation is performed by the control unit 5. FIG. 20 is a flowchart showing an operation for correcting a distortion in a light intensity distribution in the Raman spectroscopic microscope 200 according to the second exemplary embodiment.

Step S1

Firstly, in order to correct a distortion in a light intensity distribution, a light intensity distribution of a reference sample that uniformly emits light is measured. As a sufficiently-thin reference sample that uniformly emits light, for example, a fluorescent film can be used, making it possible to obtain a light intensity distribution having a high S/N ratio.

Step S2

The measured light intensity distribution of the reference sample including a distortion (hereinafter referred to as a "reference sample light intensity distribution") is divided into a plurality of sections in the horizontal-axis direction. Note that the light intensity distribution is divided so that each divided section overlaps a neighboring section(s) by 50%. An example in which the reference sample light intensity distribution is divided into eight sections is explained hereinafter.

Step S3

A Fourier transform is performed for each section of the reference sample light intensity distribution. By doing so, a spatial frequency appearing in the light intensity distribution of each section is acquired.

Step S4

Figure 21:
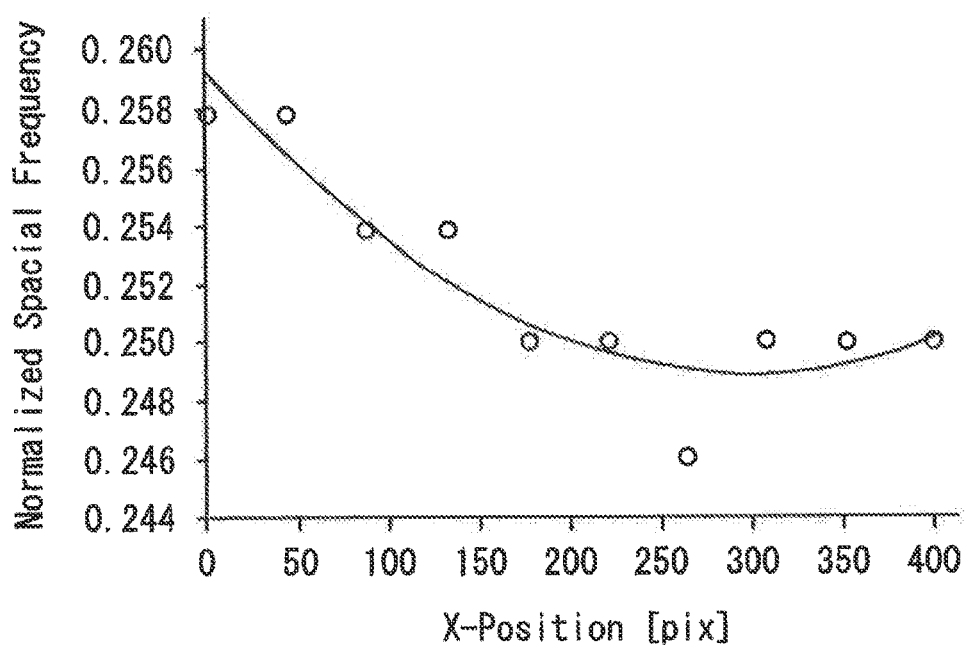
FIG. 21 is a graph in which a spatial frequency appearing in a light intensity distribution of each divided section is plotted.

The spatial frequency appearing in the light intensity distribution of each section is plotted and a value at each plotted point is interpolated. FIG. 21 is a graph in which the spatial frequency appearing in the light intensity distribution of each divided section is plotted. In FIG. 21, a polynomial approximating curve for the plotted points is shown.

Step S5

A normalized reference value for the spatial frequency is determined from the plot result. In this example, the reference value is set to 0.25 around which a lot of plotted points are present.

Step S6

Figure 22:
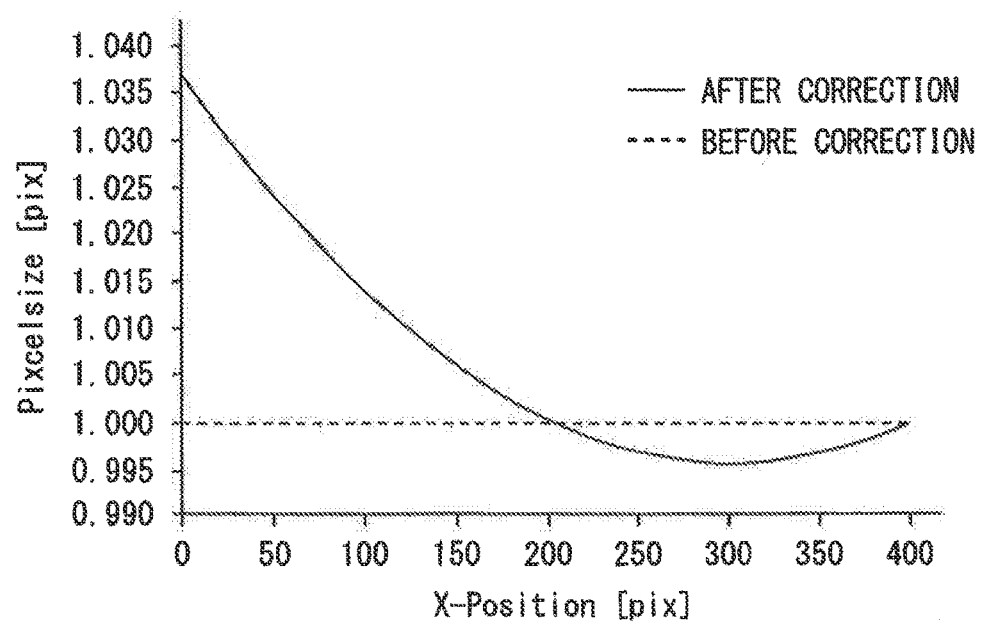
FIG. 22 is a graph showing corrections of a pixel size based on the plot result shown in FIG. 21.

A pixel size in the light intensity distribution is corrected based on the previously-determined reference value. FIG. 22 is a graph showing corrections of a pixel size based on the plot result shown in FIG. 21. In FIG. 22, a broken line represents an uncorrected pixel size (i.e., a pixel size before a correction is made) and a solid line indicates corrected pixel sizes.

Step S7

Next, a sample to be measured is measured and a light intensity distribution of the sample (referred to as an "uncorrected light intensity distribution") is measured. At this point, no pixel correction has been performed yet on the light intensity distribution of the sample and hence the light intensity distribution includes a distortion.

Step S8

Figure 23:
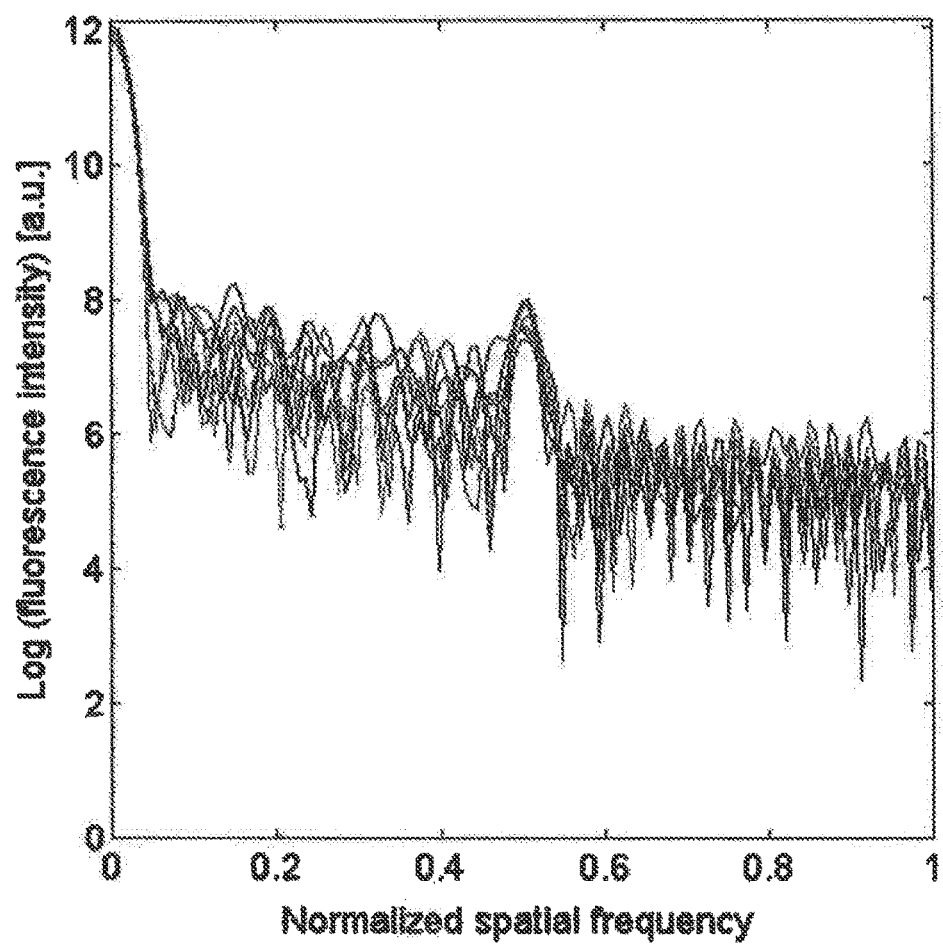
FIG. 23 shows a distortion-corrected light intensity distribution in the Raman spectroscopic microscope according to the second exemplary embodiment.

The corrected pixel size determined in the step S6 is applied to the uncorrected light intensity distribution acquired in the step S7. By doing so, the pixel size in the light intensity distribution shown in FIG. 18 (i.e., the uncorrected light intensity distribution), that is, a spatial pitch in the X-axis direction of the light intensity distribution is corrected. FIG. 23 shows the distortion-corrected light intensity distribution in the Raman spectroscopic microscope 200 according to the second exemplary embodiment. In this way, the spatial frequency appearing in the light intensity distribution of the spectrally-dispersed Raman scattered light becomes constant and the distortion included in the light intensity distribution is removed.

Figure 24:
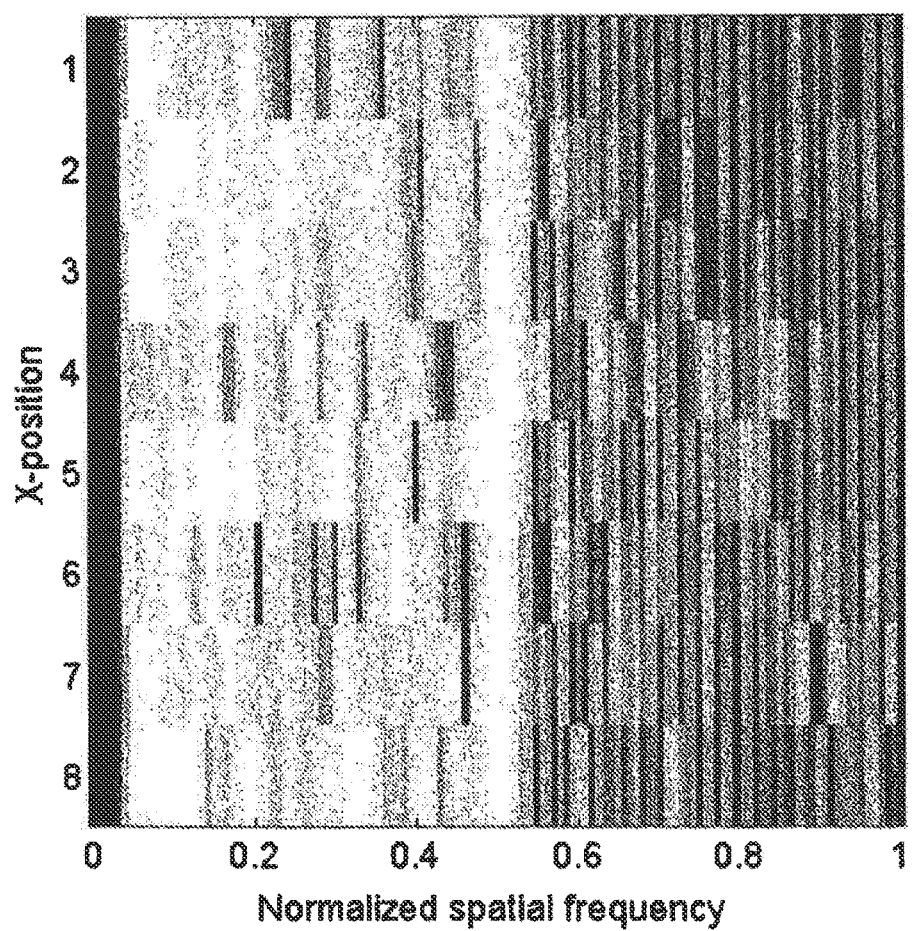
FIG. 24 shows a 2D distribution of light intensities obtained from the distortion-corrected light intensity distribution shown in FIG. 23.

Hereinafter, the light intensity distribution of the sample for which the pixel size (the spatial pitch) has been corrected is referred to as a "corrected light intensity distribution". FIG. 24 shows a 2D distribution of light intensities obtained from the corrected light intensity distribution shown in FIG. 23. In FIG. 19, the part having a strong light intensity appearing at or near the normalized spatial frequency of 0.5 shifts to the negative side as the value indicating the place in the Y-axis direction increases. In contrast to this, in FIG. 24, it can be confirmed that the shift of the part having the strong light intensity appearing at or near the normalized spatial frequency of 0.5 to the negative side is smaller than the shift in FIG. 19. That is, it can be understood that the 2D image of the object to be observed acquired based on the uncorrected light intensity distribution is shift-corrected and an accurate 2D image of the object to be measured can be thereby obtained. Note that the horizontal axis in FIG. 24 indicates normalized spatial frequencies.

Note that it is also possible to remove or reduce the distortion included in the light intensity distribution of the spectrally-dispersed Raman scattered light by using a spectroscope having no aberration. However, a high cost is required to construct a spectroscope having no aberration. In addition, since it requires a sophisticated manufacturing technique and hence requires a long time for the manufacturing. In contrast to this, the correction of the distortion in the light intensity distribution according to this exemplary embodiment can be carried out only by the calculation performed by the control unit 5. Therefore, since the distortion in the 2D image can be corrected without using a special spectroscope, it is easily implemented for a Raman spectroscopic microscope and it is also advantageous in view of the reduction in cost.

Note that the present invention is not limited to the aforementioned exemplary embodiments and may be modified as appropriate without departing from the spirit of the present invention. For example, the above-described configurations of the optical system 3 and the spectroscope 4 are merely examples. That is, the configurations of the optical system and the spectroscope can be modified as desired, provided that they can provide functions similar to those of the optical system 3 and the spectroscope 4.

Although an example in which the light intensity distribution is divided into eight sections is explained in the second exemplary embodiment, the number of sections into which the light intensity distribution is divided can be any number no less than two. Further, each section does not necessarily have to overlap a neighboring section(s) and the overlapping ratio does not necessarily have to be 50%. Further, changes in the spatial frequency along the X-axis may be continuously obtained by continuously moving the section in which the spatial frequency is obtained. In such a case, an appropriate window function such as a Hanning window can be used.

In the above-described exemplary embodiments, an improvement in the spatial resolution on the observation plane (i.e., the X-Y plane) is described. However, it is also possible to improve a spatial resolution in the depth direction of a sample (i.e., the Z-axis direction perpendicular to the X-Y plane, i.e., perpendicular to the observation plane) by using the 0th order diffracted light and the +1st and −1st order diffracted lights. Specifically, it is possible to form interference fringes in the depth direction of a sample by appropriately adjusting the phase and the intensity of the 0th order diffracted light with respect to the +1st and −1st order diffracted lights and making them interfere with each other. In this way, it is possible to improve the spatial resolution in the depth direction of the sample, based on a principle similar to that for the observation plane, by combining a plurality of images observed at different Z-coordinates.

Note that the above-described diffraction grating 2 can be configured so that it can be removably attached. In this way, when the diffraction grating 2 is used, the above-described structured illumination can be used, thus enabling a structured-illumination slit confocal microscope to be formed. Further, when the diffraction grating 2 is not used, it is possible to use it as an ordinary slit confocal microscope.

In the above-described exemplary embodiments, a configuration using only one galvanometer mirror 33 is used and hence the scanning by the linear illumination light LL can be performed only in the Y-axis direction. However, it is also possible to perform the scanning by the linear illumination light LL in the X-direction in addition to the Y-direction by disposing two galvanometer mirrors having scanning directions perpendicular to each other in a place in or near the position of the above-described galvanometer mirror 33. In this way, it is possible to measure a wider area of a sample.

In the above explanation, the scanning can be performed by sweeping the linear illumination light LL by using the galvanometer mirror 33 of the optical system 3. However, for example, by driving (i.e., moving) a stage on which a sample is placed while fixing the position of the linear illumination light LL, the sample can be scanned substantially by the linear illumination light LL. Note that needless to say, the scanning by the linear illumination light LL can also be performed by controlling the driving of both of the optical system 3 and the stage.

A Raman spectroscopic microscope is explained in the above-described exemplary embodiments. However, such a Raman spectroscopic microscope can be obtained by mounting an attachment for providing functions as a Raman spectroscopic microscope to an ordinary optical microscope. Specifically, among the components of the optical system 3 shown in FIG. 2, the mirror 34, the lens L3, and the objective lens OL are already provided in an ordinary optical microscope. Therefore, the components of the optical system 3 other than those optical components (i.e., the cylindrical lenses CL1 to CL3, the lenses L1, L2 and L4, the shield plate 31, the edge filter 32, and the galvanometer mirror 33) as well as the light source 1, the diffraction grating 2, the spectroscope 4, and the control unit 5 may be attached to an ordinary non-inverted/inverted optical microscope as an attachment for a Raman spectroscopic microscope.

The present invention made by the inventors of the present application has been explained above in a concrete manner based on exemplary embodiments. However, the present invention is not limited to the above-described exemplary embodiments, and needless to say, various modifications can be made without departing from the spirit and scope of the present invention.

This application is based upon and claims the benefit of priority from Japanese patent application No. 2014-165760, filed on Aug. 18, 2014, the disclosure of which is incorporated herein in its entirety by reference.

REFERENCE SIGNS LIST

1 LIGHT SOURCE
2 DIFFRACTION GRATING
3 OPTICAL SYSTEM
4 SPECTROSCOPE
5 CONTROL UNIT
10 OBJECT TO BE OBSERVED
31 SHIELD PLATE
32 EDGE FILTER
33 GALVANOMETER MIRROR
34 MIRROR
40 SLIT
41, 42 CONCAVE MIRROR
43 DISPERSIVE DEVICE
44 DETECTION UNIT
100 RAMAN SPECTROSCOPIC MICROSCOPE
200 RAMAN SPECTROSCOPIC MICROSCOPE
CL1-CL3 CYLINDRICAL LENS
L LASER LIGHT
L1-L4 LENSE
Ld ILLUMINATION LIGHT
Lr RAMAN SCATTERED LIGHT
LL LINEAR ILLUMINATION LIGHT
OL OBJECTIVE LENS

The invention claimed is:

1. A Raman spectroscopic microscope comprising:
a light source;
a diffraction device configured to diffract light emitted from the light source and thereby generate diffracted light;
a spectroscope configured to acquire a spectrum of incident light and a spatial distribution of light intensities of the spectrum;
an optical system configured to apply interference light formed by +1st order diffracted light and −1st order diffracted light generated in the diffraction device to an object to be observed as linear illumination light and guide a Raman scattered light generated by the application of the linear illumination light to the object to be observed to the spectroscope, the linear illumination light having its longitudinal direction in a first direction perpendicular to interference fringes formed by the interference light; and
a controller configured to cause the optical system to scan the object to be observed with the linear illumination light in a second direction perpendicular to the first direction, wherein
the controller scans the object to be observed by the linear illumination light in such a manner that a sampling interval in the second direction coincides with a spatial frequency appearing in an intensity distribution in the first direction of the linear illumination light.

2. The Raman spectroscopic microscope according to claim 1, wherein
the spectroscope comprises:
a slit on which the Raman scattered light is incident; and
an image pickup device configured so that the Raman scattered light that enters the image pickup device through the slit forms an image on an image pickup surface thereof, and a spectrum of the Raman scattered light and a spatial distribution of light intensities of the spectrum are acquired by performing an image-shooting by the image pickup device.

3. The Raman spectroscopic microscope according to claim 1, wherein the light that is emitted from the light source and is incident on the diffraction device is collimated light.

4. The Raman spectroscopic microscope according to claim 1, further comprising a beam cross-section converter disposed between the light source and the diffraction device or in the optical system, the beam cross-section converter being configured to change a shape of a beam cross-section of light passing therethrough.

5. A Raman spectroscopic microscope comprising:
a light source;
a diffraction device configured to diffract light emitted from the light source and thereby generate diffracted light;
a spectroscope configured to acquire a spectrum of incident light and a spatial distribution of light intensities of the spectrum;
an optical system configured to apply interference light formed by +1st order diffracted light and −1st order diffracted light generated in the diffraction device to an object to be observed as linear illumination light and guide a Raman scattered light generated by the application of the linear illumination light to the object to be observed to the spectroscope, the linear illumination light having its longitudinal direction in a first direction perpendicular to interference fringes formed by the interference light;
a controller configured to cause the optical system to scan the object to be observed with the linear illumination light in a second direction perpendicular to the first direction; and
an actuator configured to move the diffraction device, wherein
the controller controls the actuator to move a position of the diffraction device to change a phase of the interference fringes formed by the interference light formed by the +1st and −1st order diffracted lights in a multi-step manner while maintaining an irradiation place of the linear illumination light with respect to the object to be observed,
the spectroscope obtains a plurality of spectrums,
each of the plurality of spectrums is obtained for a respective one of the changed phases of the interference fringes and
the controller generates a spatial distribution of light intensities of a spectrum in the irradiation place by combining spatial distributions of light intensities of the plurality of spectrums obtained by the spectroscope.

6. A Raman spectroscopic microscope comprising:
a light source;
a diffraction device configured to diffract light emitted from the light source and thereby generate diffracted light;
a spectroscope configured to acquire a spectrum of incident light and a spatial distribution of light intensities of the spectrum;
an optical system configured to apply interference light formed by +1st order diffracted light and −1st order diffracted light generated in the diffraction device to an object to be observed as linear illumination light and guide a Raman scattered light generated by the application of the linear illumination light to the object to be observed to the spectroscope, the linear illumination light having its longitudinal direction in a first direction perpendicular to interference fringes formed by the interference light; and
a controller configured to cause the optical system to scan the object to be observed with the linear illumination light in a second direction perpendicular to the first direction, wherein
the controller acquires a spatial distribution of light intensities of the spectrum of the Raman scattered light acquired by the spectroscope, and
the controller corrects a spatial pitch of the spatial distribution of light intensities so that a spatial frequency appearing in the spatial distribution of light intensities becomes uniform.

7. The Raman spectroscopic microscope according to claim 6, wherein the controller:
divides the spatial distribution of light intensities acquired by the spectroscope into a plurality of sections;
acquires a spatial frequency appearing in a spatial distribution of light intensities for each of the plurality of sections;
determine a reference value based on the spatial frequencies that are respectively acquired for each of the plurality of sections; and
corrects the spatial distribution of light intensities of the spectrum by correcting a size of each pixel of the spatial distribution based on the reference value.

8. A Raman spectroscopic microscope comprising:
a light source;
a diffraction device configured to diffract light emitted from the light source and thereby generate diffracted light;
a spectroscope configured to acquire a spectrum of incident light and a spatial distribution of light intensities of the spectrum;
an optical system configured to apply interference light formed by +1st order diffracted light and −1st order diffracted light generated in the diffraction device to an object to be observed as linear illumination light and guide a Raman scattered light generated by the application of the linear illumination light to the object to be observed to the spectroscope, the linear illumination light having its longitudinal direction in a first direction perpendicular to interference fringes formed by the interference light; and
a controller configured to cause the optical system to scan the object to be observed with the linear illumination light in a second direction perpendicular to the first direction, wherein
a phase and an intensity of 0th order diffracted light generated in the diffraction device are adjusted with respect to a phase of the +1st and −1st order diffracted lights, and the +1st and −1st order diffracted lights and the 0th order diffracted light are thereby made to interfere with each other so that interference fringes are formed in a depth direction of a sample.

9. A Raman scattered light observation method comprising:
diffracting light emitted from a light source by a diffraction device and thereby generating diffracted light;
applying interference light formed by +1st order diffracted light and −1st order diffracted light generated in the diffraction device to an object to be observed as linear illumination light having its longitudinal direction in a first direction perpendicular to interference fringes formed by the interference light;

scanning the object to be observed by the linear illumination light in a second direction appendicular to the first direction; and acquiring a spectrum of Raman scattered light generated by the application of the linear illumination light to the object to be observed and a spatial distribution of light intensities of the spectrum, wherein the object to be observed is scanned by the linear illumination light in such a manner that a sampling interval in the second direction coincides with a spatial frequency appearing in an intensity distribution in the first direction of the linear illumination light.

10. The Raman scattered light observation method according to claim 9, wherein the Raman scattered light is made incident on a slit, an image is formed on an image pickup surface of an image pickup device by the Raman scattered light that enters the image pickup device through the slit, and a spectrum of the Raman scattered light and a spatial distribution of light intensities of the spectrum are acquired by performing an image-shooting by the image pickup device.

11. The Raman scattered light observation method according to claim 9, wherein the light that is emitted from the light source and is incident on the diffraction device is collimated light.

12. The Raman scattered light observation method according to claim 9, wherein a beam cross-section converter is disposed on a light-source side of the diffraction device or on a side of the diffraction device opposite to the light-source side thereof, the beam cross-section converter being configured to change a shape of a beam cross-section of light passing therethrough.

13. A Raman scattered light observation method comprising:

diffracting light emitted from a light source by a diffraction device and thereby generating diffracted light;

applying interference light formed by +1st order diffracted light and −1st order diffracted light generated in the diffraction device to an object to be observed as linear illumination light having its longitudinal direction in a first direction perpendicular to interference fringes formed by the interference light;

scanning the object to be observed by the linear illumination light in a second direction appendicular to the first direction; and acquiring a spectrum of Raman scattered light generated by the application of the linear illumination light to the object to be observed and a spatial distribution of light intensities of the spectrum, wherein a phase of the interference fringes formed by the interference light formed by the +1st and −1st order diffracted lights is changed in a multi-step manner while maintaining an irradiation place of the linear illumination light with respect to the object to be observed, and a spatial distribution of light intensities of a spectrum in the irradiation place is generated by combining spatial distributions of light intensities of a plurality of spectrums, each of the plurality of spectrums being obtained for a respective one of the changed phases of the interference fringes.

14. A Raman scattered light observation method comprising:

diffracting light emitted from a light source by a diffraction device and thereby generating diffracted light;

applying interference light formed by +1st order diffracted light and −1st order diffracted light generated in the diffraction device to an object to be observed as linear illumination light having its longitudinal direction in a first direction perpendicular to interference fringes formed by the interference light;

scanning the object to be observed by the linear illumination light in a second direction appendicular to the first direction; and acquiring a spectrum of Raman scattered light generated by the application of the linear illumination light to the object to be observed and a spatial distribution of light intensities of the spectrum, wherein a spatial pitch of the spatial distribution of light intensities of the spectrum of the Raman scattered light is corrected so that a spatial frequency appearing in the spatial distribution of light intensities becomes uniform.

15. The Raman scattered light observation method according to claim 14, wherein the spatial distribution of light intensities of the spectrum of the Raman scattered light is divided into a plurality of sections, a spatial frequency appearing in a spatial distribution of light intensities is acquired for each of the plurality of sections, a reference value is determined based on the spatial frequencies that are respectively acquired for each of the plurality of sections, and the spatial distribution of light intensities of the spectrum is corrected by correcting a size of each pixel of the spatial distribution based on the reference value.

16. A Raman scattered light observation method comprising:

diffracting light emitted from a light source by a diffraction device and thereby generating diffracted light;

applying interference light formed by +1st order diffracted light and −1st order diffracted light generated in the diffraction device to an object to be observed as linear illumination light having its longitudinal direction in a first direction perpendicular to interference fringes formed by the interference light;

scanning the object to be observed by the linear illumination light in a second direction appendicular to the first direction; and acquiring a spectrum of Raman scattered light generated by the application of the linear illumination light to the object to be observed and a spatial distribution of light intensities of the spectrum, wherein a phase and an intensity of 0th order diffracted light generated in the diffraction device are adjusted with respect to a phase of the +1st and −1st order diffracted lights, and the +1st and −1st order diffracted lights and the 0th order diffracted light are thereby made to interfere with each other so that interference fringes are formed in a depth direction of a sample.

* * * * *